United States Patent
Bonutti et al.

[11] Patent Number: 5,961,499
[45] Date of Patent: Oct. 5, 1999

[54] EXPANDABLE CANNULA

[75] Inventors: Peter M. Bonutti, 1303 W. Evergreen Plz., Effingham, Ill. 62401; James S. Hawkins, Houston, Tex.

[73] Assignee: Peter M. Bonutti, Effingham, Ill.

[21] Appl. No.: 08/467,698

[22] Filed: Jun. 6, 1995

Related U.S. Application Data

[60] Continuation-in-part of application No. 08/254,368, Jun. 6, 1994, Pat. No. 5,573,517, which is a division of application No. 08/013,942, Feb. 4, 1993, Pat. No. 5,320,611.

[51] Int. Cl.$^6$ .................................................. A61M 25/04
[52] U.S. Cl. ............................ 604/272; 604/96; 604/282; 606/194; 606/198
[58] Field of Search .................................. 606/198, 194; 604/52, 53, 282, 272, 96

[56] References Cited

U.S. PATENT DOCUMENTS

| | | |
|---|---|---|
| 319,296 | 6/1885 | Molesworth . |
| 668,879 | 2/1901 | Miller . |
| 702,789 | 6/1902 | Gibson . |
| 2,566,499 | 9/1951 | Richter . |
| 3,788,318 | 1/1974 | Kim et al. . |
| 3,789,852 | 2/1974 | Kim et al. . |
| 3,811,449 | 5/1974 | Gravlee et al. . |
| 3,968,800 | 7/1976 | Vilasi . |
| 4,183,102 | 1/1980 | Guiset . |
| 4,320,762 | 3/1982 | Bentov . |
| 4,461,281 | 7/1984 | Carson . |
| 4,504,268 | 3/1985 | Herlitze . |
| 4,589,868 | 5/1986 | Dretler . |
| 4,630,609 | 12/1986 | Chin . |
| 4,685,458 | 8/1987 | Leckrone ........................... 606/159 X |
| 4,706,670 | 11/1987 | Andersen et al. . |
| 4,716,901 | 1/1988 | Jackson et al. . |
| 4,846,812 | 7/1989 | Walker et al. . |
| 4,899,729 | 2/1990 | Gill et al. . |
| 4,954,126 | 9/1990 | Wallsten . |
| 4,966,583 | 10/1990 | Debbas . |
| 4,998,539 | 3/1991 | Delsanti . |
| 5,037,404 | 8/1991 | Gold et al. . |
| 5,041,093 | 8/1991 | Chu . |
| 5,069,674 | 12/1991 | Fearnot et al. . |
| 5,183,464 | 2/1993 | Dubrul et al. . |
| 5,197,971 | 3/1993 | Bonutti ............................... 606/198 X |
| 5,226,899 | 7/1993 | Lee et al. ................................ 604/282 |
| 5,234,425 | 8/1993 | Fogarty et al. ...................... 606/198 X |
| 5,318,588 | 6/1994 | Horzewski et al. . |

FOREIGN PATENT DOCUMENTS 184396  7/1966  U.S.S.R. .

*Primary Examiner*—Michael H. Thaler
*Attorney, Agent, or Firm*—Tarolli, Sundheim, Covell, Tummino & Szabo

[57] ABSTRACT

Cannulas for surgical and medical use expand along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening. In one embodiment of the invention, the cannula has a pointed end portion. In this embodiment of the invention, the cannula includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel. An expandable chamber may be provided at the distal end of the cannula.

45 Claims, 15 Drawing Sheets

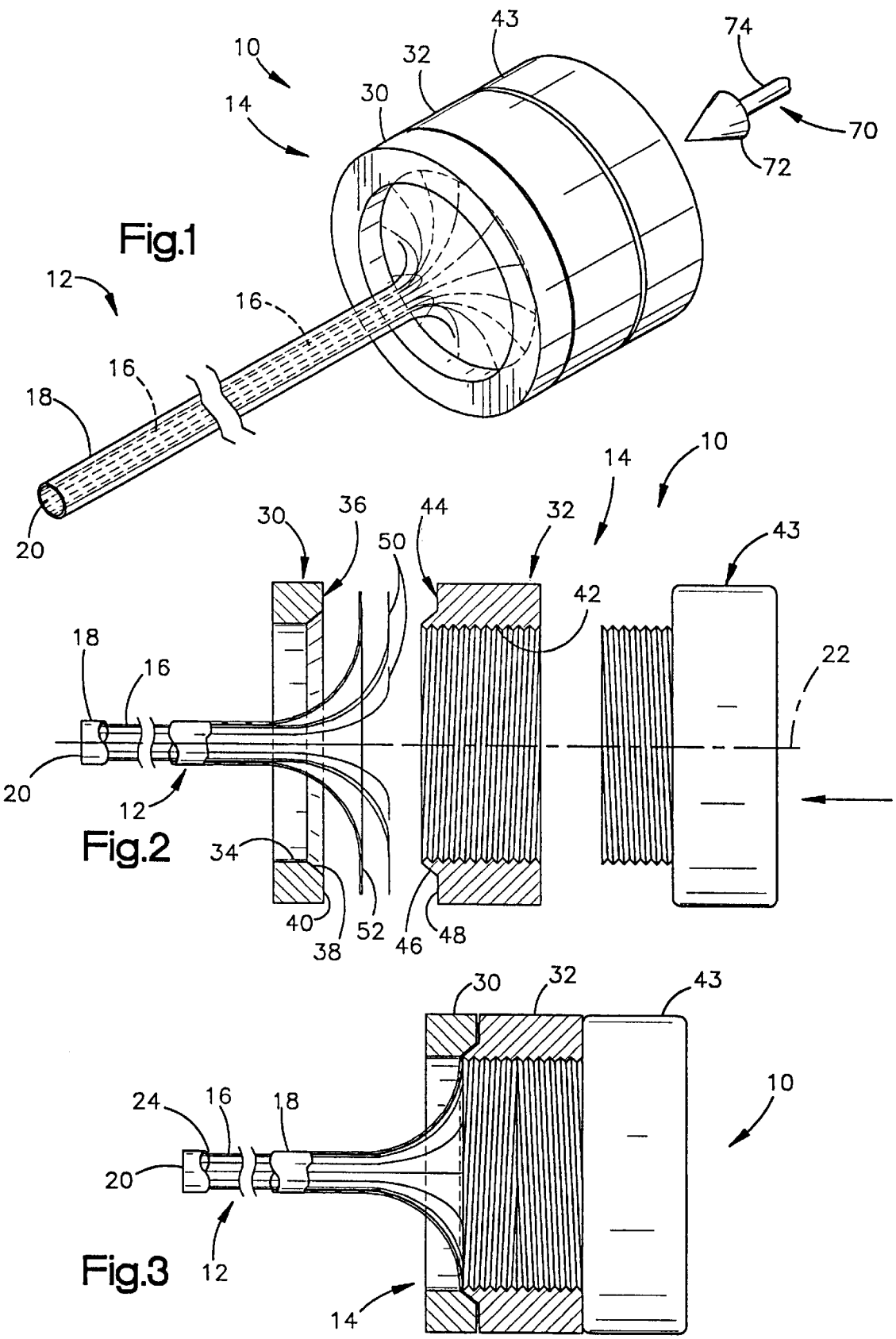

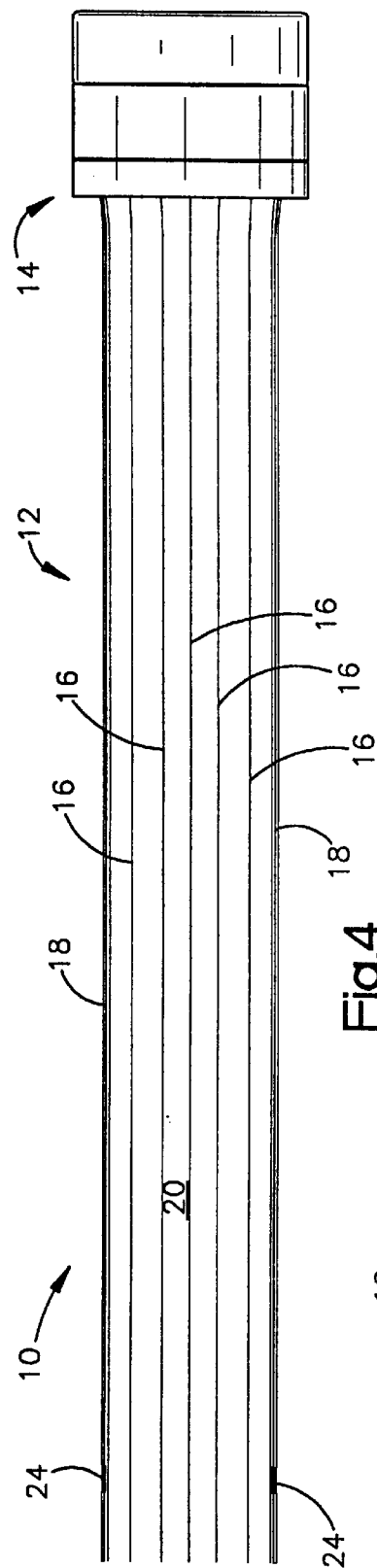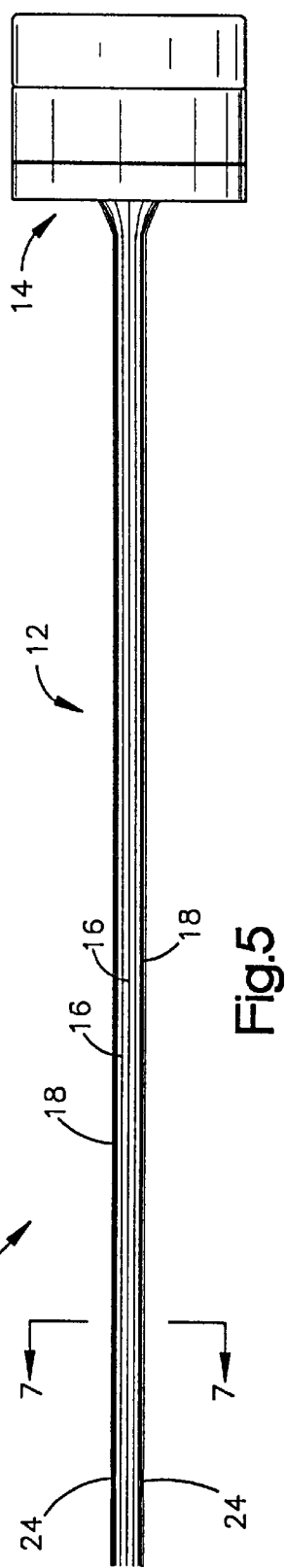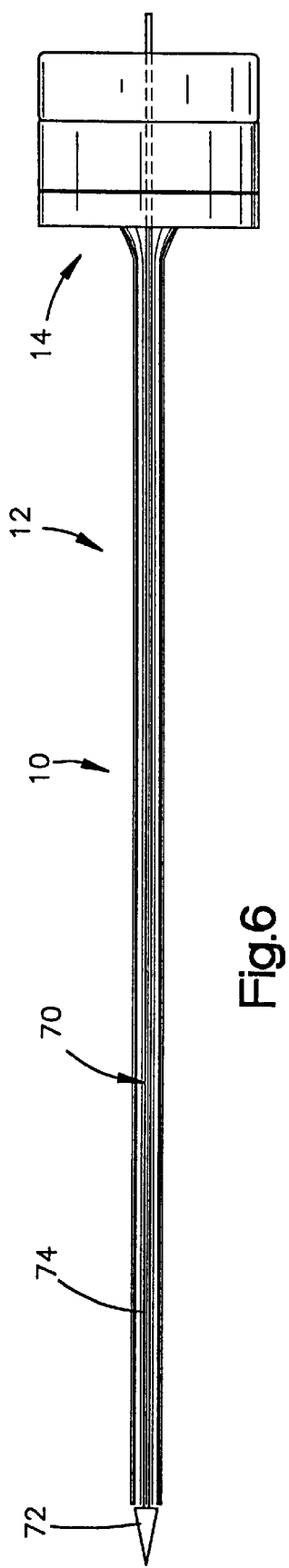

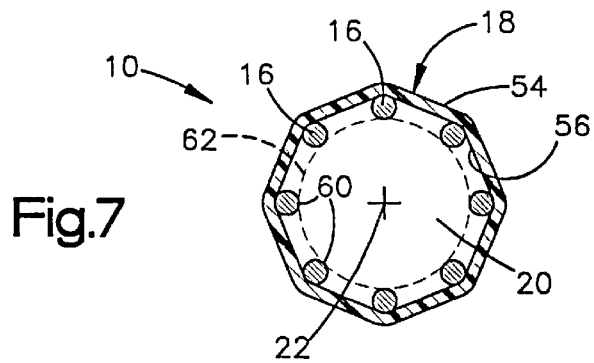
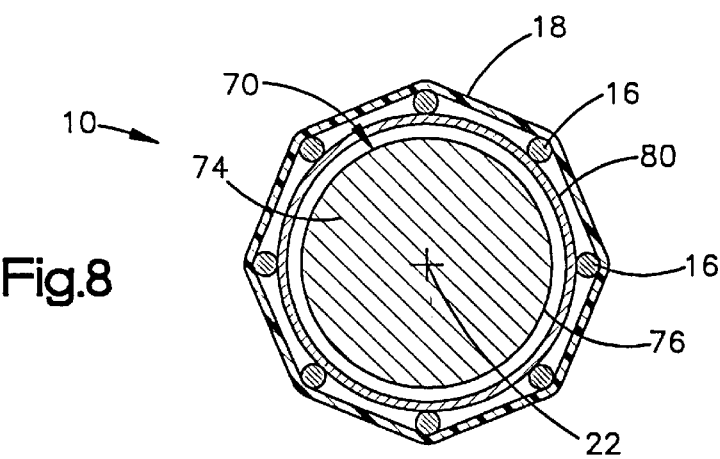
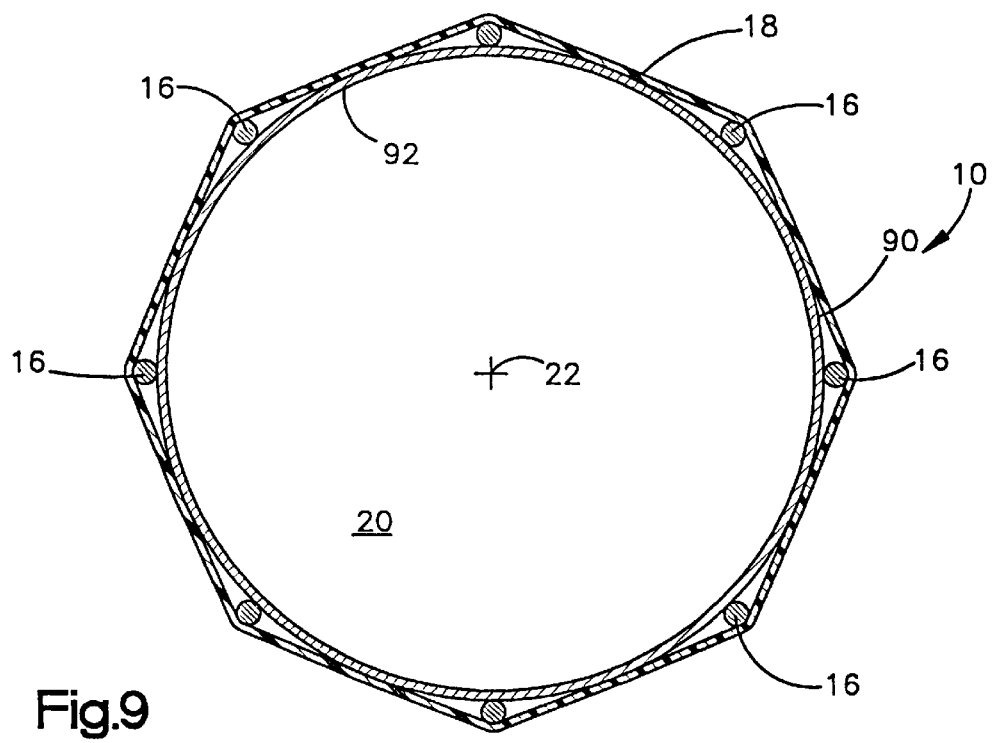

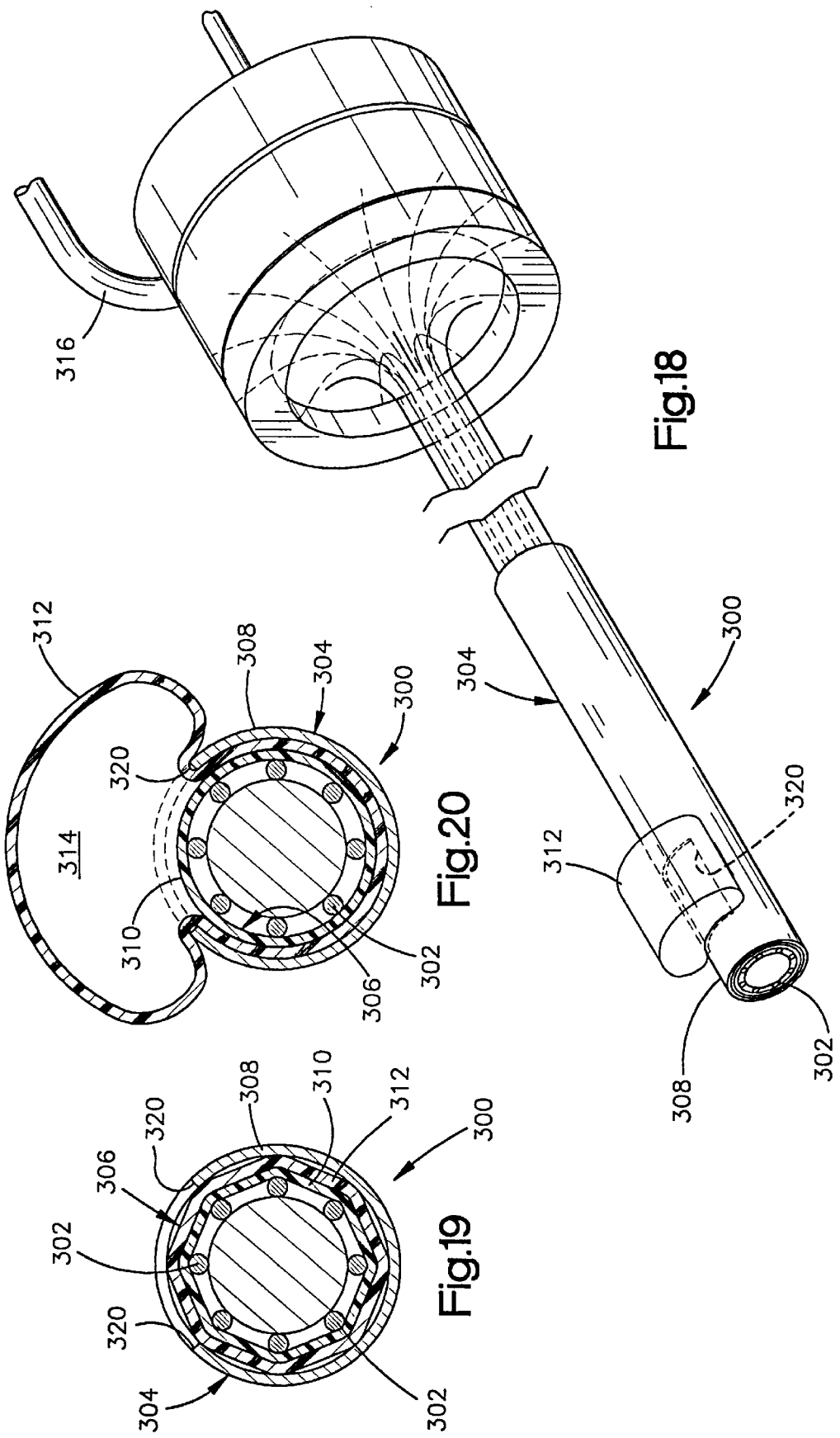

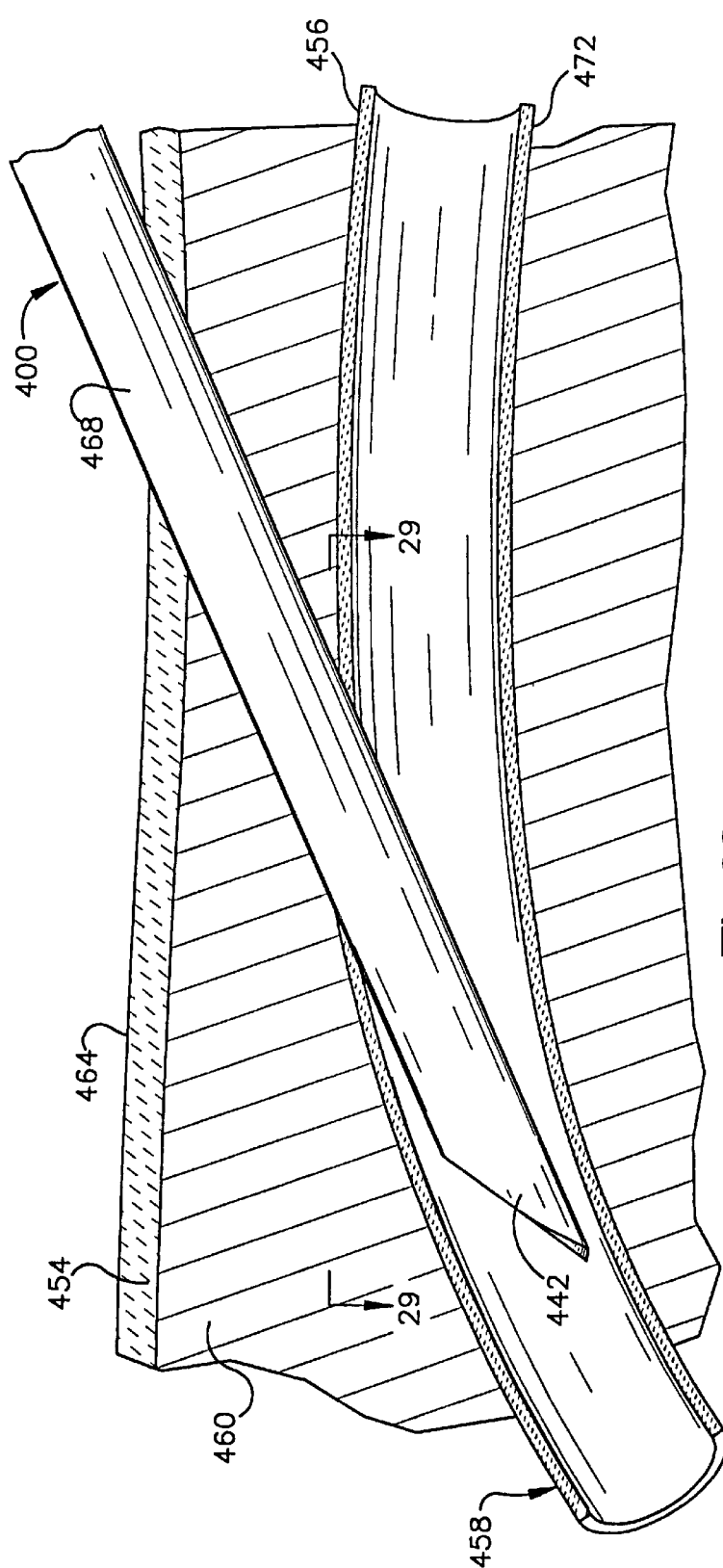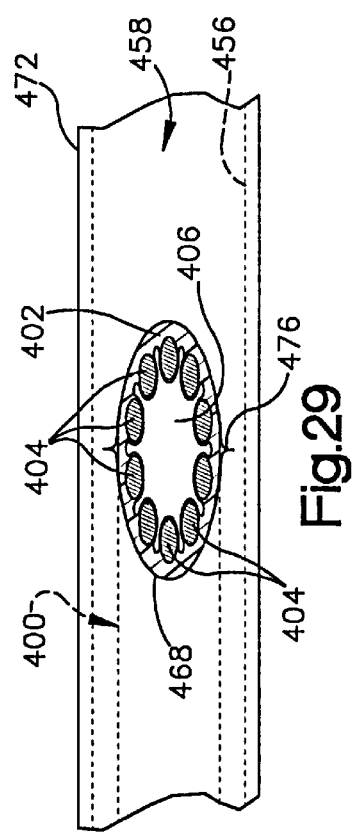

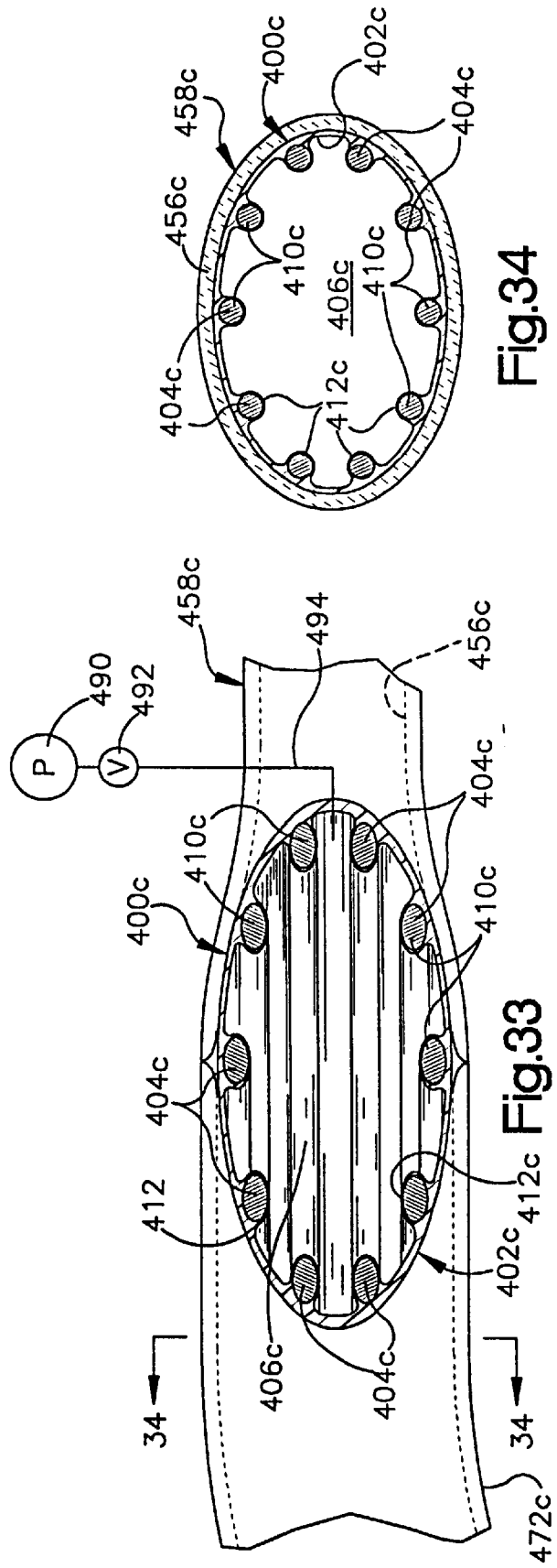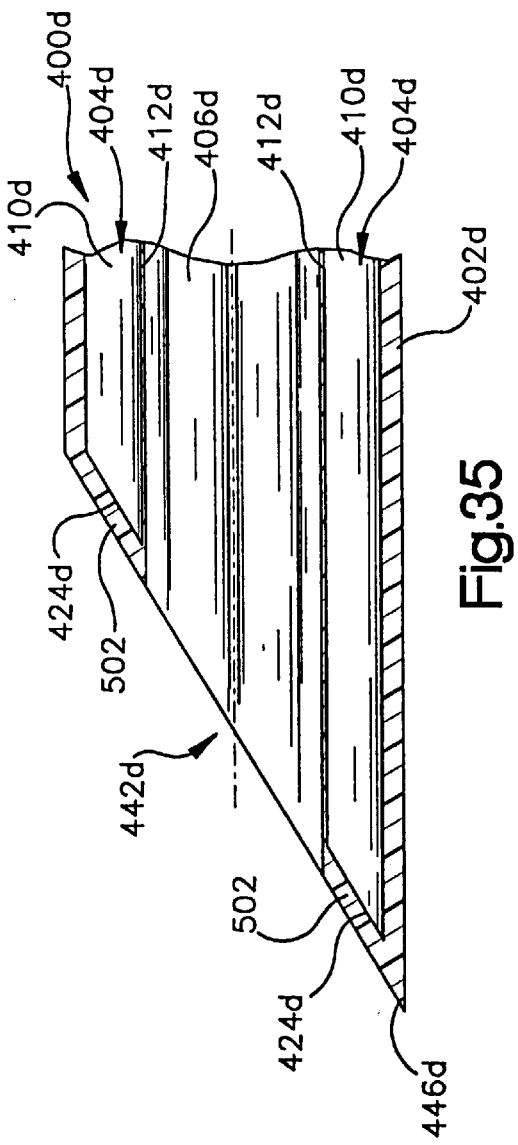

EXPANDABLE CANNULA

RELATED APPLICATION

This application is a continuation-in-part of U.S. patent application Ser. No. 08/254,368, filed Jun. 6, 1994 now U.S. Pat. No. 5,573,517. The aforementioned application Ser. No. 08/254,368 is a divisional of U.S. patent application Ser. No. 08/013,942, filed Feb. 4, 1993 (now U.S. Pat. No. 5,320, 611). The benefit of the earlier filing dates of the aforementioned application Ser. No. 08/254,368 and application Ser. No. 08/013,942 is hereby claimed for all subject matter common to this application and the aforementioned applications.

BACKGROUND OF THE INVENTION

The present invention relates to cannulas for surgical and medical use. A typical cannula is a fixed diameter tube which a surgeon uses to maintain an instrument passage through tissue to a subcutaneous working location. The surgeon must first make an incision the full depth of the cannula in order to insert the cannula. This traumatic action damages good tissue in order to get to bad tissue. It would be desirable to provide cannulas which do not require a full depth incision, or at least require only a needle-size entrance opening, and which still allow use of a cannula to maintain an instrument passage.

SUMMARY OF THE INVENTION

In accordance with one of the features of the invention, cannulas are provided which expand along their entire length. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The cannulas may be expanded by inserting members into the cannulas or by fluid pressure.

In accordance with another feature of the invention, a leading end portion of the cannula is constructed to pierce human body tissue. This enables the cannula to form its own opening in body tissue as the cannula is inserted into the tissue.

In accordance with still another feature of the invention, the cannula can be inserted into a blood vessel and expanded. A flow of fluid can be conducted through the cannula into the blood vessel.

The cannula advantageously includes a sheath which encloses a plurality of wires. A member may be inserted into the sheath and moved along the wires to expand the cannula. Each of the wires may advantageously include a core which is at least partially enclosed by a jacket which is integrally formed as one piece with the sheath. If desired, the cannula may be expanded by fluid pressure rather than inserting a member into the cannula.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is a perspective view of a cannula in accordance with a first embodiment of the invention, shown in an unexpanded condition;

FIG. 2 is an exploded longitudinal sectional view of the cannula of FIG. 1;

FIG. 3 is an assembled view of the cannula of FIG. 1;

FIG. 4 is a schematic side view illustrating the cannula of FIG. 1 in an expanded condition;

FIG. 5 is a schematic side view illustrating the cannula of FIG. 1 in a contracted or collapsed condition;

FIG. 6 is a side view similar to FIG. 5 illustrating a trocar inserted in the cannula of FIG. 1;

FIG. 7 is a sectional view taken along line 7—7 of FIG. 5;

FIG. 8 illustrates the cannula of FIG. 7 in a partially expanded condition with a trocar and a tubular insert therein;

FIG. 9 illustrates the cannula of FIG. 7 in a fully expanded condition with a larger tubular insert therein;

FIG. 18 is a perspective view of a cannula forming another embodiment of the invention;

FIG. 19 is a sectional view of the cannula of FIG. 18, the cannula being shown in a retracted condition;

FIG. 20 is a sectional view of the cannula of FIG. 18, the cannula being shown in an expanded condition;

FIG. 28 is a fragmentary schematic illustration, generally similar to FIG. 26, illustrating the relationship of the cannula to the blood vessel after the cannula has pierced the side wall of the blood vessel and has been inserted into the blood vessel with the cannula in the contracted condition of FIG. 22;

FIG. 29 is a fragmentary schematic illustration, taken generally along the line 29—29 of FIG. 28, further illustrating the relationship between the cannula and the blood vessel;

FIG. 33 is a fragmentary schematic illustration, generally similar to FIG. 31, illustrating the relationship between another embodiment of the cannula and a blood vessel after the cannula has been inserted into the blood vessel and expanded by fluid pressure;

FIG. 34 is a sectional view, taken along the line 34—34 of FIG. 33, further illustrating the relationship between the expanded cannula and the blood vessel;

FIG. 35 is a fragmentary sectional view, generally similar to FIG. 21, illustrating a pointed end portion of another embodiment of the cannula;

DESCRIPTION OF PREFERRED EMBODIMENTS

Figure 10:
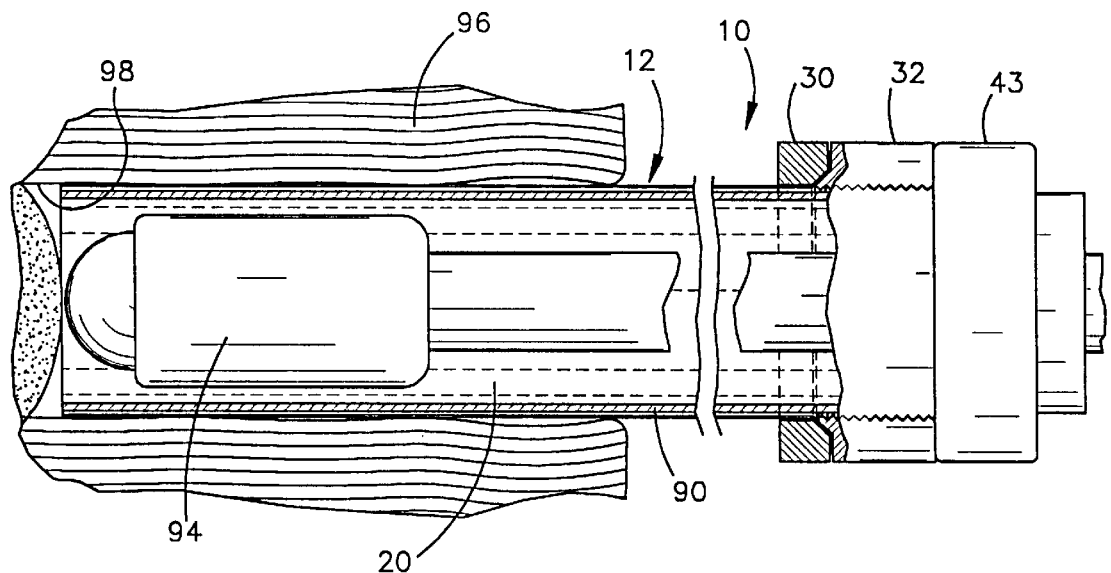
FIG. 10 illustrates the cannula of FIG. 1 in use.

In a first embodiment of the invention, a cannula 10 (FIG. 1) includes an expanding portion 12 and a proximal end portion 14. The expanding portion 12 includes a plurality of longitudinally extending wires 16. The wires 16 are surrounded for most of their length by an overlying elastic sheath 18. The wires 16 define between them a central instrument passage 20.

The wires 16 are preferably made of a material which is flexible, does not break, and does not stretch. A preferred material is music wire, which is thin gauge steel about 0.015" in diameter. The use of the term "wire" in this application and its claims does not limit the invention to metal wires. The "wires" may also be made of other elongate material such as composites or plastics or other metals. The "wires" may also be coated.

The number of wires may be selected as desired. Applicants have found that 8 to 10 wires will suffice for a cannula expandable up to 7 mm OD, and that 12 wires or more may be necessary for a larger cannula. Ten larger diameter wires (0.025") may be used rather a larger number of small diameter wires. A greater number of wires 16 can be used if a greater diameter is needed. If not enough wires 16 are used, an instrument (trocar, insert, scope, etc.) inserted through the passage 20 when the cannula 10 is expanded will contact the elastic sheath 18 rather than the wires 16, at locations between the wires.

The wires 16 are self-aligning. When the cannula 10 is in a contracted condition, the wires 16 may overlap. When the cannula 10 is expanded, the wires 16 straighten out as shown.

The elastic sheath 18 is preferably secured to the wires 16 at both proximal and distal ends, to prevent the sheath's sliding off the wires during insertion and removal of the cannula 10. Rubber cement or cyanoacrylate or a similar adhesive can be used to bond the sheath 18 to the wires 16 as shown schematically at 24.

The elastic sheath 18 is preferably made of latex or silicone, or of C-Flex®, a general purpose thermoplastic elastomer sold by Linvatec Corporation of Clearwater, Fla. The sheath 18 is of a diameter such that it is stressed even when the cannula 10 is fully contracted. Thus, the sheath 18 constantly biases the wires 16 radially inwardly toward the axis 22 of the cannula 10.

At the proximal end portion 14 of the cannula 10, the wires 16 are clamped between an inner ring member 30 and an outer ring member 32. The inner ring member 30 has a central opening 34. The inner ring member 30 has a clamping surface 36 including a beveled edge 38 and an annular radially extending surface 40. The outer ring member 32 has a threaded central opening 42 for receiving a standard luer lock 43. The outer ring member 32 has a clamping surface 44 including a beveled edge 46 and an annular radially extending surface 48.

The ring members 30 and 32 can be made of metal, in which case they can be brazed or welded together. The ring members 30 and 32 can be made of plastic, in which case then they can be UV joined or joined by adhesive.

Proximal end portions 50 of the wires 16 are trapped between the ring members 30 and 32. When the ring members 30 and 32 are joined together as in FIG. 3, the proximal end portions 50 of the wires 16 are trapped between the clamping surface 36 of the inner ring 30 and the clamping surface 44 of the outer ring 32. The proximal end portion 52 of the sheath 18 is preferably also trapped between the rings 30 and 32, to secure the sheath proximally. Alternatively, the proximal end portion 52 of the sheath 18 may be bonded to the wires 16 at a proximal location adjacent the ring members 30 and 32. Thus, the proximal end of the cannula expanding portion 12 is secured, having a large diameter generally equal to the expanded diameter of the cannula 10.

The sheath 18 has a longitudinally extending circumferential outer surface 54 (FIG. 7) and a longitudinally extending circumferential inner surface 56. The wires 16 engage the circumferential inner surface 56 of the sheath 18. The radially inner surfaces 60 of the wires 16 define an annular periphery 62 within which any item inserted in the cannula 10 is disposed. In one embodiment which has been constructed, when contracted, the cannula 10 is about 2 mm diameter, the size of a 14 ga needle. Thus, the cannula 10 can possibly be inserted as a needle, clearing its own path, and not needing a trocar first. The constructed cannula is about 90 mm long. Other useful sizes include (i) up to 2.5 mm diameter with a 70 mm length; (ii) up to 7 mm diameter with a 110 mm length; and (iii) up to 11 mm diameter with a 160 mm length.

In use of the cannula 10, the surgeon makes a small incision in the epidermis. He inserts a narrow trocar such as the trocar 70 (FIGS. 6 and 8) into the central passage 20 of the cannula 10. The pointed end portion 72 of the trocar 70 will project distally. The shaft portion 74 of the trocar 70 is disposed inside the passage 20. The outer surface 76 of the trocar shaft portion 74 engages the radially inner surfaces 60 of the wires 16. The proximal end portion 78 of the trocar 70 extends proximally from the cannula 10.

The end portion 72 of the trocar 70 may be blunt in order to push away internal tissue. In this case, a small incision would need to be made through the epidermis.

The trocar/cannula assembly is inserted through the incision in the epidermis to the subcutaneous working location. Then, a tubular insert 80 (FIG. 8) is moved distally between the wires 16 of the cannula 10 and the trocar 70. The insert 80 is preferably a hollow metal tube at least as large in ID as the OD of the trocar pointed end portion 72. The trocar 70 can then be removed from the cannula 10, leaving the cannula and the insert 80 in place in the tissue.

Because the insert 80 is larger in diameter than the trocar 70, during insertion of the insert 80, the cannula 10 is expanded radially outwardly, as seen in a comparison of FIGS. 7 and 8 (which are not necessarily to scale). The tissue around the cannula 10 is also stretched. The surgeon has thus made a larger passage for instruments, along its entire length, without cutting tissue.

After the tissue is allowed to relax, the surgeon removes the insert 80. The cannula 10 collapses radially inwardly because of the elastic sheath and because of the force of the tissue around it. But the tissue opening does not necessarily collapse completely, because of the viscoelastic nature of tissue, which tends to maintain its stretched condition for some time.

The surgeon then puts a second insert inside the cannula 10. The second insert is a hollow tube larger in diameter than the first insert 80. Again, the cannula expands radially outwardly, and the tissue stretches.

In this manner, the surgeon continues with larger and larger inserts, until the tissue opening is as large as desired. The cannula may then be in the expanded condition shown in FIG. 9, with a full size metal insert 90 within the cannula 80. The insert 90 then functions as a normal cannula, allowing insertion and removal of surgical instruments and the like.

Figure 11:
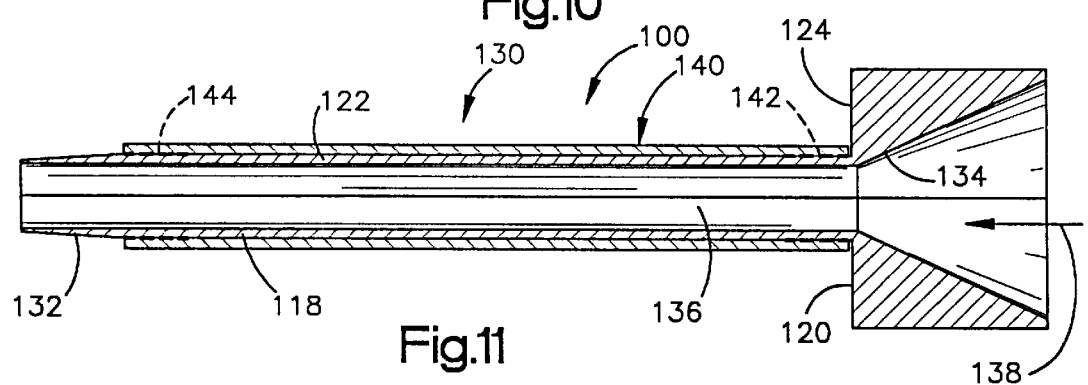
FIG. 11 is a view of a cannula in accordance with a second embodiment of the present invention, shown in an unexpanded condition.

Items inserted through the central passage 20 of the cannula 10 always contact the inner cylindrical surface 92 of the insert 90. This provides a non-wearing, slippery engagement, which is desirable for insertion and removal of the instruments. An example is illustrated in FIG. 11 showing a probe 94 extending through the central instrument passage 20 of the cannula 10 having an insert 90 therein. The cannula 10 has expanded tissue 96 radially outwardly to create a cavity 98 therein.

Items inserted through the central passage 20 of the cannula 10, such as the inserts 80 and 90, always contact the radially inner surfaces 60 of the wires 16. This also provides a non-wearing, slippery engagement, which is desirable for insertion and removal of the inserts.

The cannula 10 is discarded after use to prevent contamination.

Thus, it is seen that the wires 16 have outer surface portions 60 disposed radially inwardly in the cannula 10 and forming contact surfaces for surgical instruments and the like inserted through the central instrument passage 20 of the cannula. The sheath 18 has an outer circumferential surface 54 engaging tissue when the cannula 10 is in use. The wires 16 block engagement of instruments inserted through the central instrument passage 20 of the cannula 16 with the elastic sheath 18. The sheath 18 blocks engagement of tissue with the wires 16, and the sheath and the wires block engagement of tissue with any instruments inserted through the cannula 10.

The cannula 10 expands radially outwardly along substantially its entire length against the bias of the sheath 18. Thus, the cannula 10 can accommodate through its central instrument passage 20 a surgical instrument or the like having a diameter along its entire length which is greater than the diameter of the cannula in the contracted condition. This is not possible with cannulas which expand only along a portion of their length.

A second embodiment of the invention is illustrated in FIGS. 11–17. An expandable cannula 100 includes four longitudinally extending members 102, 104, 106, and 108. Each member includes a longitudinally extending arcuate segment and a widened proximal end portion. The members 102, 104, 106, and 108 are made of plastic. One suitable material is Delrin® brand plastic.

Specifically, the member 102 includes a longitudinally extending arcuate segment 110 and a widened proximal end portion 112. The member 104 includes a longitudinally extending arcuate segment 114 and a widened proximal end portion 116. The member 106 includes a longitudinally extending arcuate segment 118 and a widened proximal end portion 120. The member 108 includes a longitudinally extending arcuate segment 122 and a widened proximal end portion 124.

The members 102, 104, 106, and 108 each subtend an angle of 90°. When the members 102, 104, 106, and 108 are placed together, their longitudinally extending arcuate segments 110, 114, 118, and 122 form a tubular expandable cannula structure 130.

The distal ends 132 of the members 102, 104, 106, and 108 are tapered inwardly for ease of entrance through tissue. The widened proximal end portions 112, 116, 120, and 124 together form a handle for the cannula 100 which also allows entry of an instrument therethrough. The end portions have angled inner surfaces 134 to guide an instrument into the longitudinally extending central instrument passage 136 of the cannula 100 in the direction indicated by the arrow 138. The handle (proximal end) portion of the cannula 100 can be configured to attach instruments to it, or to have a cap screwed onto the end to close the cannula.

The arcuate segments 110, 114, 118, and 122 are surrounded for most of their length by an overlying elastic sheath 140. The elastic sheath 140 is secured to the segments 110, 114, 118, and 122 at proximal and distal locations 142 and 144, to prevent the sheath's sliding off the segments during insertion and removal of the cannula 100. Rubber cement or cyanoacrylate or a similar adhesive can be used to bond the sheath 140 to the segments. The elastic sheath 140 is preferably made of latex or silicone, or of the C-Flex® material described above. The sheath 140 is of a diameter such that it is stressed even when the cannula 100 is fully contracted. Thus, the sheath 140 constantly biases the segments radially inwardly toward the center of the cannula 100.

Figures 12, 13, 14:
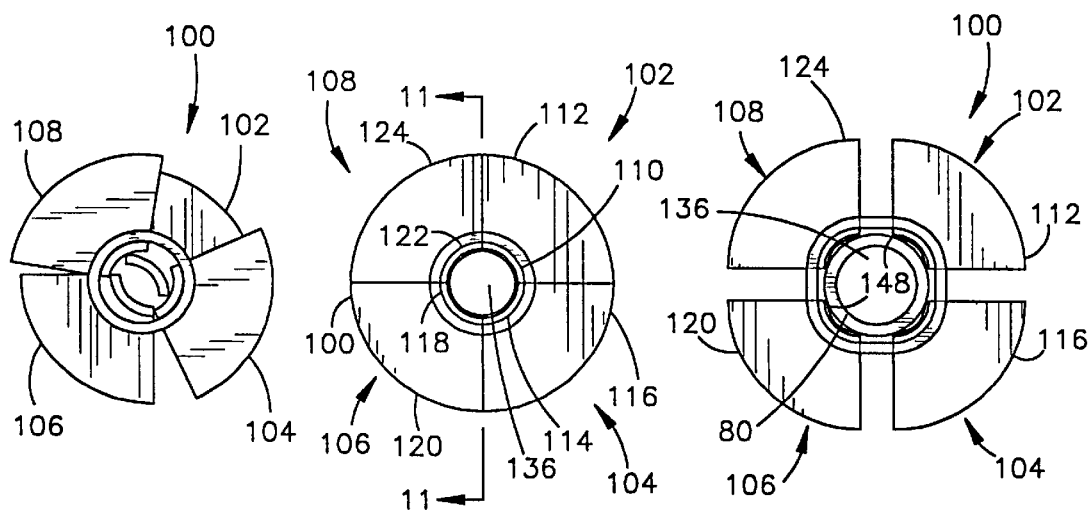
FIG. 12 is an end view of the cannula of FIG. 11 in a fully collapsed condition.
FIG. 13 is a view similar to FIG. 12 with the cannula in a partially expanded condition.
FIG. 14 is a view similar to FIG. 13 with the cannula in a fully expanded condition.
Figure 15:
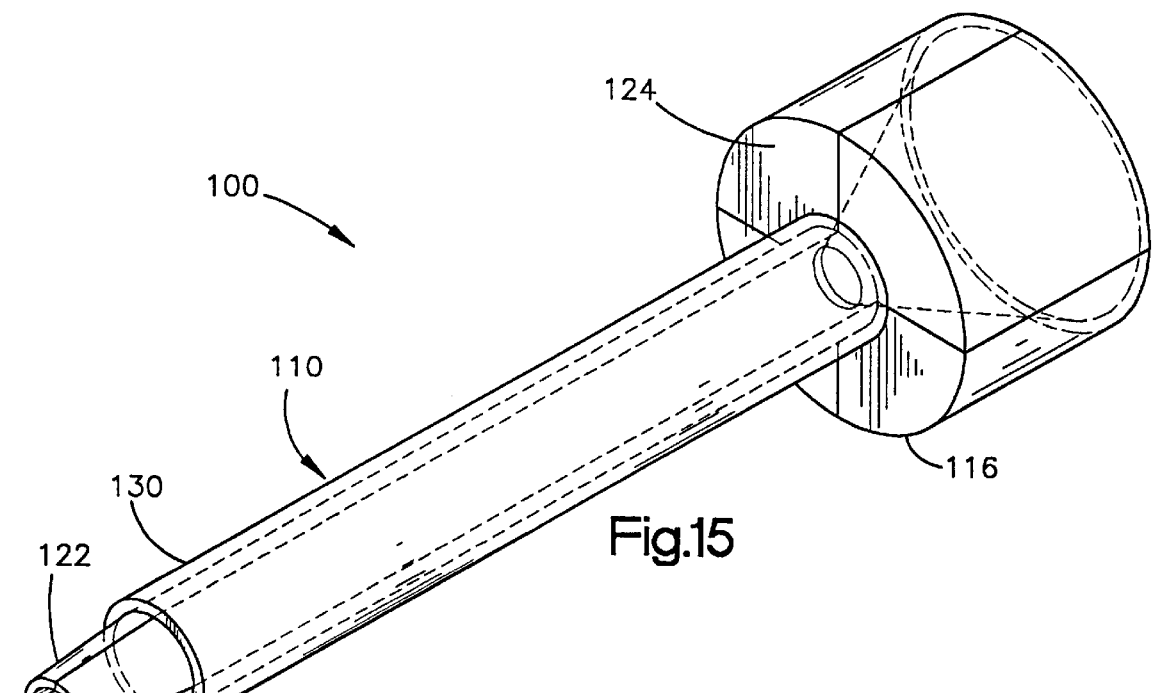
FIG. 15 is a perspective view of the cannula of FIG. 11.
Figure 16:
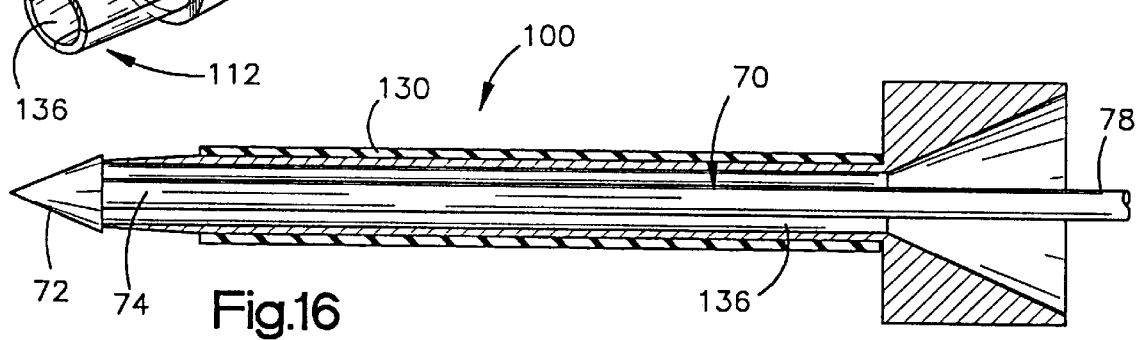
FIG. 16 illustrates the cannula of FIG. 15 with a trocar therein.
Figure 17:
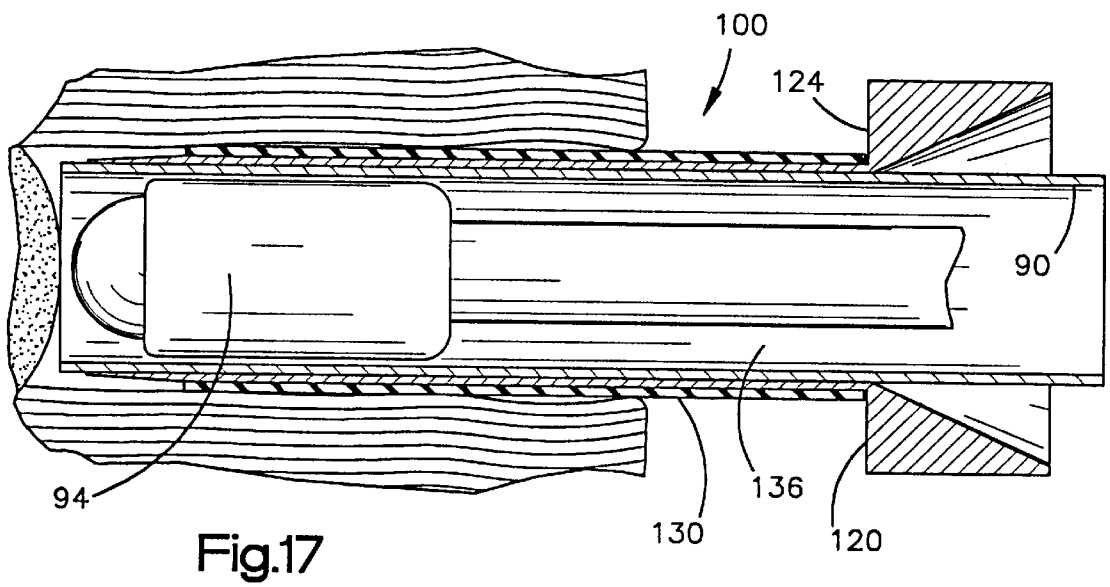
FIG. 17 illustrates the cannula of FIG. 11 in use.

One cannula that has been constructed is 90 mm in length, and about 5 mm in diameter when aligned in a tube form as shown in FIGS. 12–14. The members can collapse (overlap onto themselves as shown in FIG. 12) into a smaller diameter. The cannula can expand to about 12+mm OD.

In use of the cannula 100, the surgeon makes a small incision in the epidermis. He inserts a narrow trocar such as the trocar 70 (FIG. 16) into the central passage 136 of the cannula 100. The pointed end portion 72 of the trocar 70 will project distally. The shaft portion 74 of the trocar 70 is disposed inside the passage 136. The proximal end portion 78 of the trocar 70 extends proximally from the cannula 100.

A trocar should be used with the cannula 100 only when needed. The distal end portion of the cannula 100 is preferably used alone to push through internal tissue once an epidermal incision has been made.

The trocar/cannula assembly is inserted through the incision in the epidermis to the subcutaneous working location. Then, a tubular insert 80 (FIG. 14) is inserted longitudinally between the cannula 100 and the trocar 70. The insert 80 is preferably a hollow metal tube at least as large in ID as the OD of the trocar pointed end portion 72. The trocar 70 can then be removed from the cannula 100, leaving the cannula and the insert 80 in place in the tissue.

As the insert 80 is inserted in the cannula 100, the outer surface of the insert engages longitudinally extending radially inner edges 148 of the members 102, 104, 106, and 108. Because the insert 80 is larger in diameter than the trocar 70, during insertion of the insert, the cannula 100 is expanded radially outwardly, as seen in a comparison of FIGS. 13 and 14 (which are not necessarily to scale). The four members 102, 104, 106, and 108 move radially outwardly away from each other. The passage 136 is enlarged. The tissue around the cannula 100 is also stretched. The surgeon has thus made a larger passage for instruments, along its entire length, without cutting tissue.

After the tissue is allowed to relax, the surgeon removes the insert 80. The cannula 100 collapses radially inwardly because of the elastic sheath and because of the force of the tissue around it. But the tissue opening does not necessarily collapse completely, because the tissue is viscoelastic.

The surgeon then puts a second insert 90 (FIG. 17) inside the cannula 100. The second insert 90 is a hollow tube larger in diameter than the first insert 80. Again, the cannula 100 expands further radially outwardly, and the tissue stretches. The surgeon continues with larger and larger inserts, until the tissue opening is as large as desired. The cannula may then be in the expanded condition shown in FIG. 17, with the insert 90 within the cannula 100. The cannula 100 can then be removed proximally, leaving the insert in place. The insert then functions as a normal cannula, allowing insertion and removal of surgical instruments and the like such as the probe illustrated schematically at 94.

The cannula 100 expands radially outwardly along substantially its entire length against the bias of the sheath 130. Thus, the cannula 100 can accommodate through its central instrument passage 136 a surgical instrument or the like having a diameter along its entire length which is greater than the diameter of the cannula in the contracted condition. This is not possible with cannulas which expand only along a portion of their length.

It is contemplated that one would use two different size cannulas 100 to obtain a desired range of expansion. A first, smaller size, would extend from an OD of 2.5 mm to an ID of 7 mm, being about 70 mm in length. A second, larger size, would extend from an OD of 6 mm to an ID of 12 mm, being about 150 mm in length.

The expandable cannulas of the present invention may be designed to selectively expand at a location at or near the distal end. This is illustrated in FIGS. 18–20. An expandable cannula 300 similar to the expandable cannula 10 (FIGS. 1–9) includes a plurality of longitudinally extending wires 302. Instead of an elastic sheath like the sheath 18 (FIGS. 1–9), the cannula 300 includes an inflatable sheath 304. The sheath 304 includes an inner sheath member 306 and an outer sheath member 308.

The inner sheath member 306 is of a double-walled construction, including an inner wall 310 and an outer wall 312. An inflation volume 314 separates the inner wall 310 and the outer wall 312. Fluid under pressure such as air, saline, etc. may be introduced into the inflation volume 314 through a fluid port 316. The inner sheath member 306 overlies the wires 302.

When fluid under pressure is introduced into the inflation volume 314 through the fluid port 316, the outer wall 312 of the inner sheath member 306 expands radially outwardly, as shown in FIG. 20. Radially outward expansion of the outer wall 312 of the inner sheath member 306 is limited by the outer sheath member 308. The outer sheath member 308 is a single-layer sheath overlying the inner sheath member 306. A notch 320 is cut out of the outer sheath member 308. The outer wall 312 of the inner sheath member 306 can expand radially outwardly only at the location of the notch 320 in the outer sheath member 308.

The notch 320, or any similar opening in the outer sheath member 308, may be placed at or near the distal end of the cannula 300. This will stabilize the cannula 300 in the tissue, at the closest possible location to the work area off the distal end of the cannula.

In the embodiment of the invention illustrated in FIGS. 21–31, the cannula of FIGS. 1–10 has been provided with a pointed distal or leading end portion to facilitate the piercing of human body tissue with the end portion of the cannula. In addition, each of the wires includes a core and a coating or jacket which is integrally formed as one piece with the plastic sheath of the cannula. It is contemplated that the embodiment of the cannula illustrated in FIGS. 21–31 will be particularly advantageous for use in establishing communication with interior of a vessel, such as a sac, organ, tube, duct or canal. However, the cannula may be used to establish communication with any desired portion of the human body.

The cannula 400 (FIGS. 21, 22 and 23) has the same general construction as the cannula 10 of FIGS. 1–10. Thus, the cannula 400 includes an elastic sheath 402 which encloses a plurality of longitudinally extending wires 404. The wires define between them a central passage 406 through which instruments may be inserted into a human body or fluid may be conducted into the human body. At a proximal end portion (not shown) of the cannula 400, the sheath 402 and wires 404 are clamped between ring members in the same manner illustrated in FIGS. 2 and 3 for the cannula 10.

Figure 21:
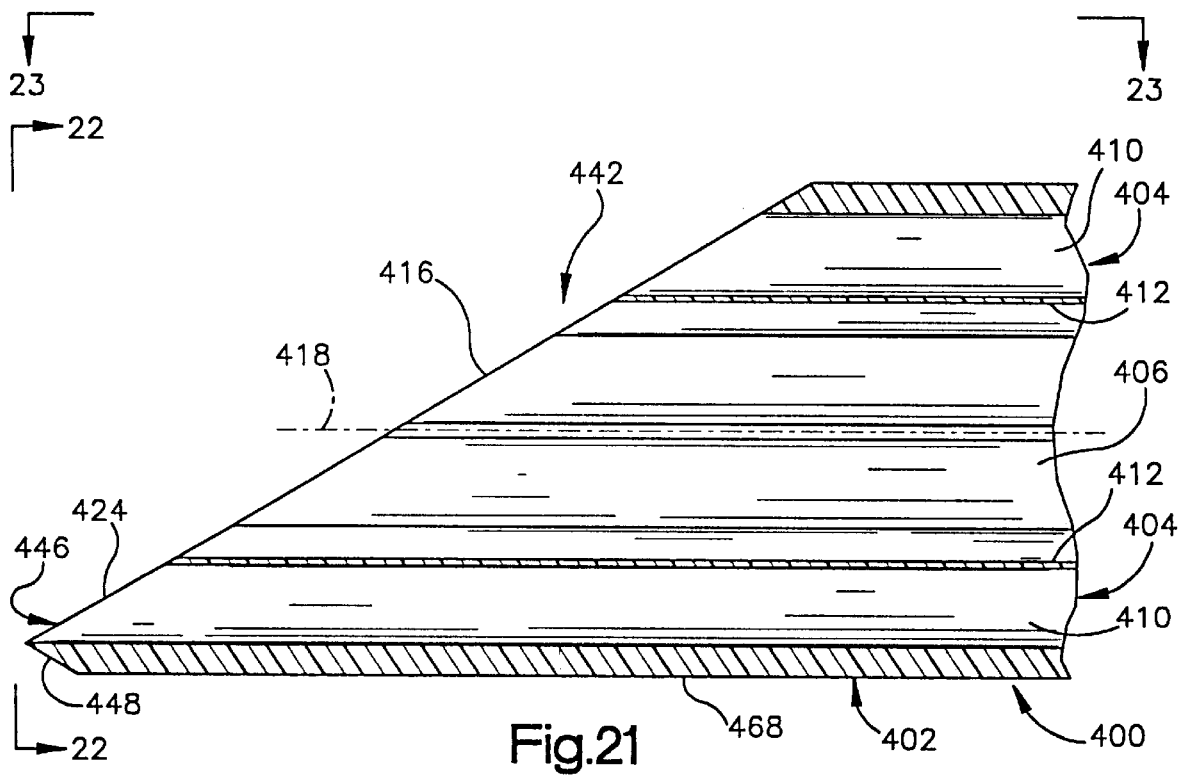
FIG. 21 is an enlarged fragmentary sectional view of a pointed end portion of another embodiment of the cannula of FIG. 1.
Figure 22:
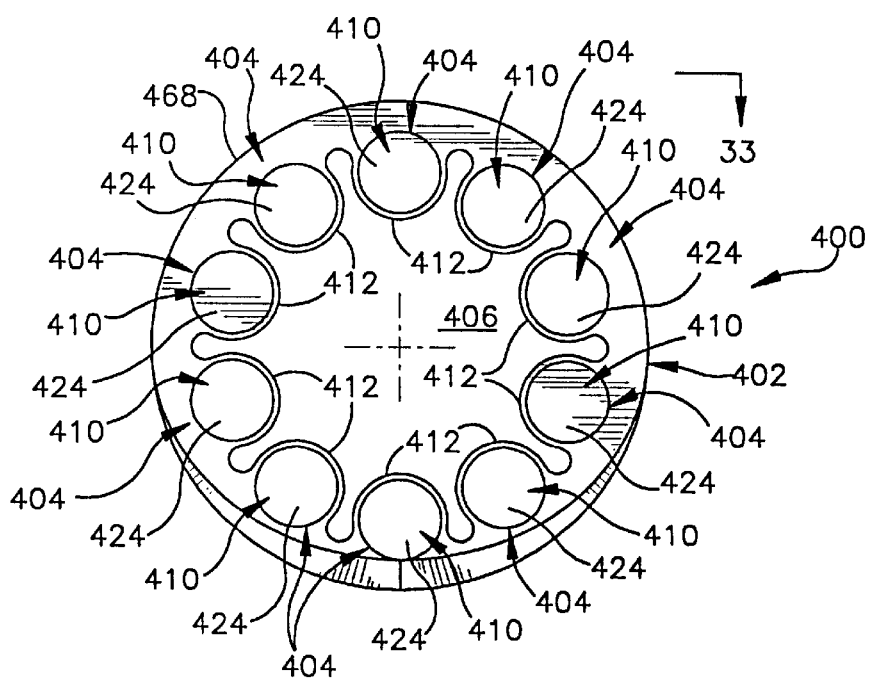
FIG. 22 is an end view, taken generally along the line 22—22 of FIG. 21, illustrating the relationship between a sheath and wires in the pointed end portion of the cannula.
Figure 23:
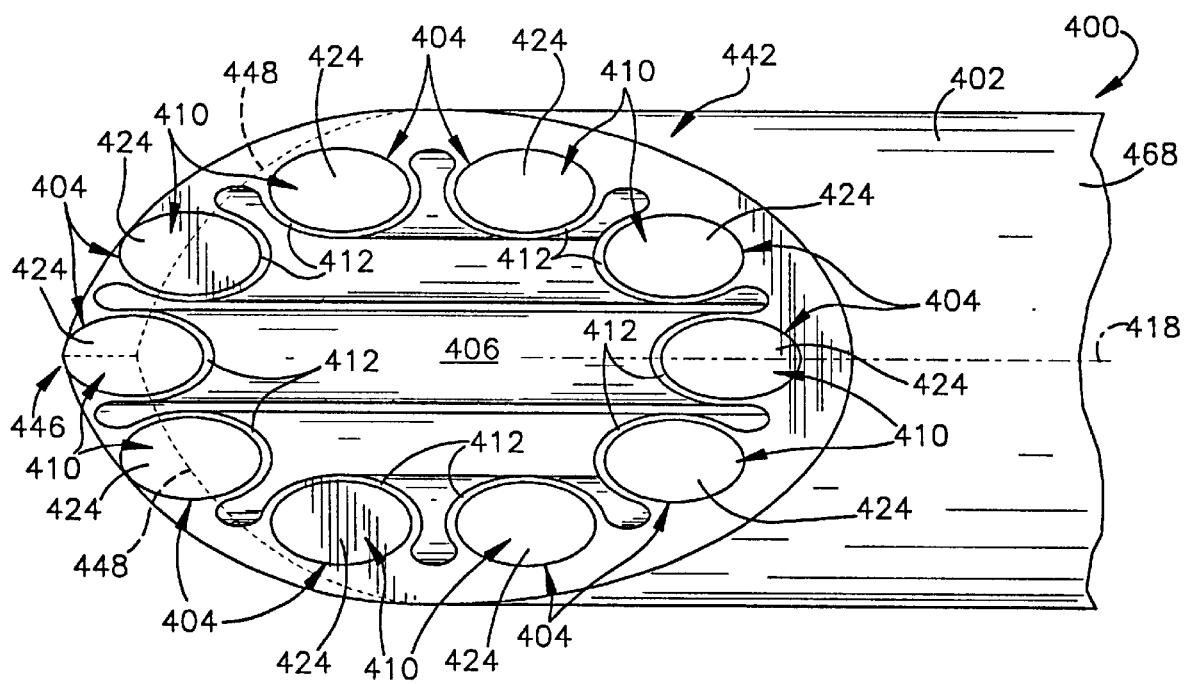
FIG. 23 is a fragmentary plan view, taken generally along the line 23—23 of FIG. 21, further illustrating the construction of the pointed end portion of the cannula.

In accordance with one of the features of the embodiment of the invention illustrated in FIGS. 21–23, each of the wires 404 includes a core 410 (FIG. 22) which is at least partially enclosed by a coating or jacket 412. The cores 410 and jackets 412 extend between opposite ends of the sheath 402. Thus, the cores 410 and jackets 412 extend from a generally circular opening 416 (FIG. 21) at the distal or leading end of the sheath 402 to clamping ring members at the proximal end (not shown) of the sheath.

The jacket 412 around the core 410 of each of the wires 404 is integrally formed as one piece with the sheath 402. Thus, each of the jackets 412 is formed of the same elastic material as the sheath 402. The elastic polymeric material of the sheath and the jackets 412 may be molded or extruded around the cores 410 during formation of the cannula 400.

Each of the jackets 412 has a longitudinal central axis which extends parallel to a longitudinal central axis 418 of the cannula 400. The jackets 412 extend throughout the entire length of the sheath 402. Since the jackets 412 are integrally formed as one piece with the sheath 402, the wires 404 are maintained in a parallel relationship with the longitudinal central axis 418 of the cannula 400. The parallel wires 404 extend from the opening 416 at the distal end of the sheath 402 to the location where the proximal end of the sheath is clamped between ring members in a manner similar to that illustrated in FIGS. 2 and 3. The wires 404 do not intersect.

Central cores 410 of the wires 404 may be formed of any desired material. In the embodiment of the invention illustrated in FIGS. 21–31, the cores 410 are formed of metal. Thus, the cores 410 are formed of music wire, that is a thin gauge steel of about 0.015 inches in diameter. However, the cores 410 could be formed of composite polymeric materials if desired. For example, the cores 410 could be formed by a matrix of polymeric material strengthened by longitudinally extending carbon fibers.

In the illustrated embodiment of the invention, the parallel cores 410 of the wires 404 have a cylindrical configuration. Thus, each of the cores 410 has a circular cross sectional configuration as viewed in a plane extending perpendicular to a longitudinal central axis of the core. In the embodiment of the invention illustrated in FIGS. 21–23, the sheath 402 engages longitudinally extending side portions of the cores 410. The longitudinally extending side portions of the cores 410 which are engaged by the sheath 402 face radially outward away from the central axis 418 of the cannula 400.

The surface portions of the cores 410 which do not engage the sheath 402 are enclosed by the jackets 412. Since the jackets 412 are integrally formed as one piece with the sheath 402, there is no precise line of demarcation between the jackets and the sheath. However, the jackets 412 extend inward from the sheath 402 toward the central axis 418 of the cannula 400 and cooperate with the sheath to enclose each of the cores 410. If desired, the jackets 412 could extend completely around the cores 410.

Circular axial end faces 424 of the cores 410 are exposed at opposite ends of the sheath 402. Thus, at the distal end of the cannula 400, the circular end faces 424 (FIGS. 22 and 23) of the cores are visible. The jackets 412 extend from the end faces 424 of the cores 410 to the opposite end of the sheath 402.

Figure 24:
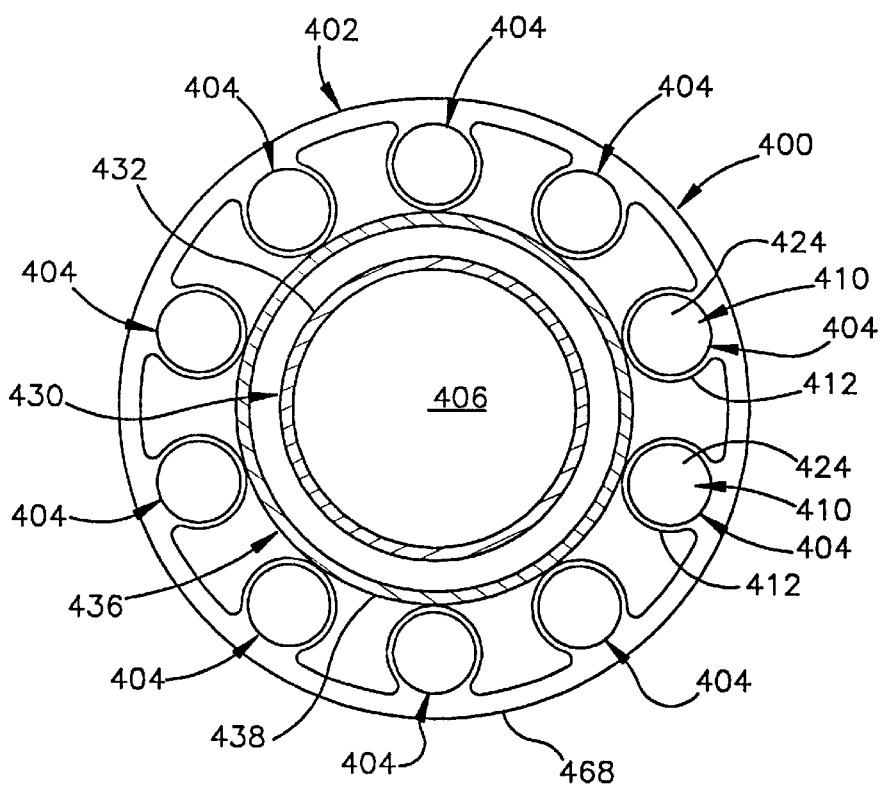
FIG. 24 is a schematic sectional view illustrating the manner in which the cannula is expanded from the contracted condition of FIG. 22 by insertion of tubular members into the cannula.

The cannula 400 is expandable throughout its length from a contracted condition (FIG. 22) to an expanded condition (FIG. 24) in the same manner as in which the cannula 10 of FIGS. 1–10 is expandable. When the cannula 400 is to be expanded from the contracted condition of FIG. 22, a first cylindrical tubular member 430 is axially inserted into the central passage 406 through the proximal end portion of the cannula 400 (FIG. 24). As the first tubular member 430 is inserted into the cannula 400, a cylindrical outer side surface 432 on the tubular member 430 slides along the wires 404 toward the distal or leading end of the cannula. Thus, the outer side surface 432 of the tubular member 430 slides on surfaces of the jackets 412 which enclose the cores 410 of the wires 404.

As the tubular member 430 is axially moved into the cannula 400 from the proximal end portion (not shown) of the cannula to the distal end portion, the wires 404 are forced radially outward away from the longitudinal central axis 418 of the cannula. Thus, the cylindrical outer side surface 432 of the member 430 applies radially outward force against the wires 404. This radially outward force is transmitted through the wires 404 to the sheath 402. As this occurs, the elastic material of the sheath 402 is resiliently stretched and the distance between the wires 404 increases.

There is minimal resistance to axial sliding movement of the tubular member 430 into the cannula 400. This is because the tubular member 430 is engaged by only the jackets 412 on the wires 404 along very thin linear areas. The outer side surface 432 of the tubular member 430 is maintained in a spaced apart relationship with the inner side surface of the sheath 402 by the wires 404. Once the tubular member 430 has been inserted into the cannula 400, the sheath 402 presses the jackets 412 on the wires 404 against the outer side surface 432 of the tubular member 430. The first tubular member 430 has a length which is greater than the length of the sheath 402 and extends axially outward from opposite ends of the sheath.

If the central passage through the tubular member 430 has sufficient cross sectional area, the cannula 400 may be used with the tubular member 430 holding the cannula in an expanded condition. However, it is believed that it may be desirable to further expand the cannula 400. Therefore, a second cylindrical tubular member 436 is inserted into the cannula 400 through the proximal end of the cannula to further expand the cannula. The second tubular member 436 has an inside diameter which is larger than the outside diameter of the first cylindrical tubular member 430.

As the second tubular member 436 is inserted into the proximal end of the cannula 400, a cylindrical outer side surface 438 on the second tubular member 436 slides along the wires 404. The second tubular member 436 forces the wires 404 radially outward away from the cylindrical outer side surface 432 of the first tubular member 430. As this occurs, the elastic material of the sheath 402 is further resiliently stretched by the force applied against the wires 404 by the tubular member 436.

As the resilient material of the cylindrical sheath 402 is circumferentially stretched, the distance between the parallel wires 404 increases. Sliding of the tubular member 436 from the proximal end to the distal end of the cannula 400 is relatively easy since the tubular member slides along the jackets 412 on the wires 404 and does not engage the inner side surface of the sheath 402. The second cylindrical tubular member 436 extends axially outward from opposite ends of the sheath 402.

Once the second cylindrical tubular member 436 has been telescopically inserted into the cannula 400 around the first or inner tubular member 430, the first tubular member can be axially withdrawn from the cannula 400. This results in the cylindrical central passage 406 through the cannula 400 having a diameter equal to the inside diameter of the relatively large second tubular member 436.

If desired, a still larger tubular member may be telescopically inserted into the cannula 400 around the second tubular member 436 to further expand the cannula and increase the size of the central passage 436 through the cannula. It is possible to expand the cannula 400 to any one of may different sizes depending upon the size of the tubular member which is used to apply force against the wires 404 and resiliently stretch the sheath 402 of the cannula. It is believed that it will be preferred to have the extent of expansion of the sheath 402 be less than the elastic limit of the material forming the sheath.

Since the elastic limit of the material forming the sheath 402 is not exceeded by expanding the cannula 400 by insertion of the members 430 and 436, when the members are withdrawn from the cannula, the sheath will resiliently contract back to the original size shown in FIG. 22. Thus, to contract the cannula 400 back to its original size, it is merely necessary to axially pull the tubular member 436 out of the proximal end of the cannula. The elastic material of the sheath 402 will move the wires 404 radially inward toward the longitudinal central axis 418 of the cannula and return the cannula back to the retracted condition shown in FIG. 22.

In accordance with one of the features of this embodiment of the invention, the cannula 400 has a pointed distal end portion 442 (FIG. 21). The pointed distal end portion 442 of the cannula 400 facilitates piercing of body tissue with the cannula. The pointed end portion 442 is formed by cutting the materials of the sheath 402 and wires 404 at an acute angle to the longitudinal central axis 418 of the cannula 400. In the embodiment of the invention illustrated in FIGS. 21 and 23, the pointed end portion 442 of the cannula 400 is formed by cutting the material of the sheath 402 and wires 404 at an angle of approximately 30° to the longitudinal central axis 418 of the cannula. Of course, the pointed end portion 442 could be skewed at a different angle relative to the longitudinal central axis 418 of the cannula 400 if desired.

The ends of the wires 404 and the end of the sheath 402 cooperate to provide the cannula 400 with an end portion 442 which can cut body tissue when the end portion of the cannula is pressed against the body tissue. The sheath 402 may advantageously be cut away adjacent to an apex 446 of the pointed end portion 442. Thus, a bevelled surface 448 is formed in the material of the sheath 402 adjacent to the apex 446 of the pointed end portion 442. The bevelled surface 448 makes the pointed end portion 442 of the cannula sharper to facilitate severing the body tissue. The bevelled surface 448 extends outward to a leading end of a wire 404 which extends through the central part of the apex 446 of the pointed end portion 442 of the cannula 400.

In the illustrated embodiment of the invention, the cylindrical cores 410 of the parallel wires 404 are formed by thin gauge steel wire. The leading end of the core 410 of the wire 404 extends through the apex 446 of the pointed end portion 442 of the cannula 400. The leading end of the core 410 of the wire 404 through the apex 446 provides a relatively sharp cutting edge at the axially outer end of the cannula 400. This sharp cutting edge can readily penetrate relatively tough body tissue.

When the pointed end portion 442 of the contracted cannula 400 is pressed against an imperforate surface area on body tissue, force is transmitted axially through the wires 404 and through the sheath 402 to the body tissue. The apex 446 of the pointed end portion penetrates the body tissue and initiates the formation of an opening in the body tissue. The initiating of the opening in the body tissue is facilitated by having the exposed relatively sharp end of the core 410 of the wire 404 which extends through the apex 446 of the pointed end portion 442 of the contracted cannula 400 engage the body tissue to initially cut the imperforate surface area of the body tissue. The leading edge portions of the sheath disposed adjacent to opposite sides of the wire 404 through the apex 446 of the cannula 400 are then effective to sever body tissue to increase the size of the opening in the body tissue.

As the contracted cannula 400 is further inserted into the body tissue, the leading end portions of additional wires 404 and leading edges of segments of the sheath 402 disposed between the wires sever the body tissue to increase the size of the opening. Thus, the sheath 402 and ends of the wires 404 cooperate to form an opening in the body tissue at a location where there was no natural opening. The size of the opening formed in the body tissue by the pointed end portion 442 of the cannula 400 increases until the opening is large enough to accept the cylindrical outer side surface of the cannula when it is in the contracted condition of FIG. 22.

Once the contracted cannula 400 has been inserted for a desired distance into the body tissue, the cannula is expanded from the contracted condition of FIG. 22 to the expanded condition of FIG. 24. As this occurs, the viscoelastic material of the body tissue is resiliently stretched and the size of the small opening formed by the cannula 400 in its contracted condition is increased. When the cannula 400 is in the expanded condition of FIG. 24 and the first or inner member 430 has been removed, surgical tools and/or optical instruments can be inserted through the cylindrical passage 406 within the second tubular member 436 and expanded cannula 400. When the expanded cannula 400 is subsequently contracted and removed from the body tissue, the viscoelastic body tissue also contracts. Therefore, the size of the wound in the body tissue is minimized.

It is contemplated that the cannula 400 will have many different uses, including the establishment of communication with the interior of many different types of vessels in a human body. For example, the cannula could be used to establish communication with the interior of a vessel such as a lung, heart, endolymphatic duct or sac, a hernial sac, or a bladder. It is also contemplated that the cannula 400 will be used as a passage through body tissue for many different types of instruments and/or fluids. For example, the cannula 400 may be used to facilitate laproscopic or arthroscopic surgery. However, it is believed that the cannula 400 will be particularly advantageous in establishing communication with the interior of a blood vessel.

Figure 26:
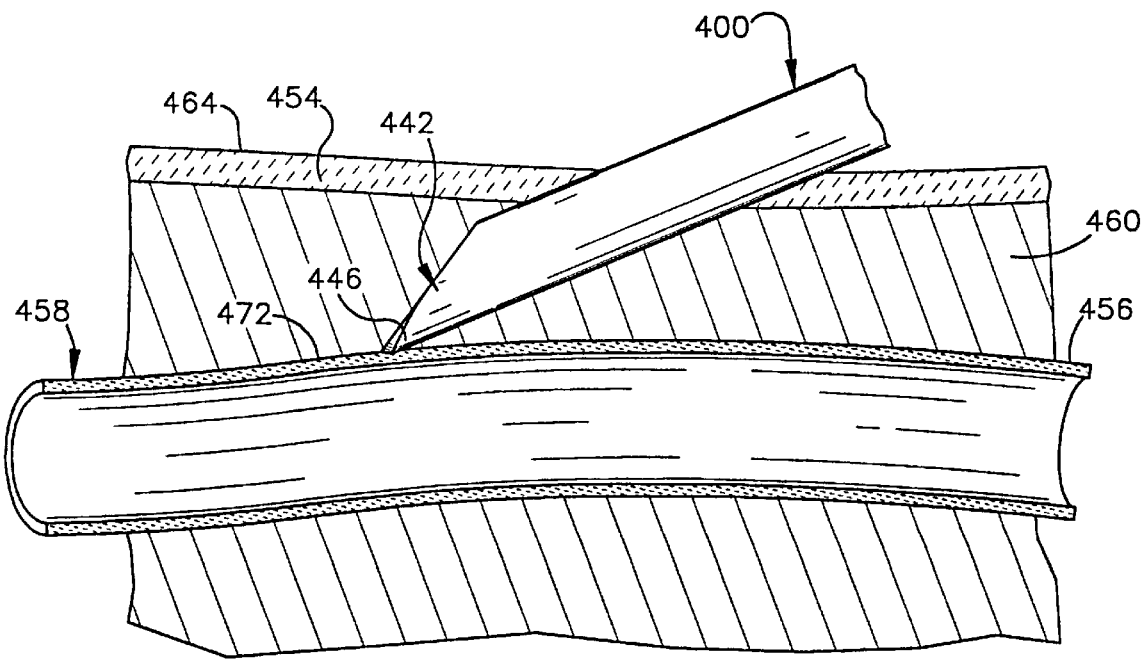
FIG. 26 is a fragmentary schematic illustration depicting the relationship between the contracted cannula and a blood vessel after the cannula has pierced skin and body tissue adjacent to the blood vessel and prior to piercing of a side wall of the blood vessel.
Figure 27:
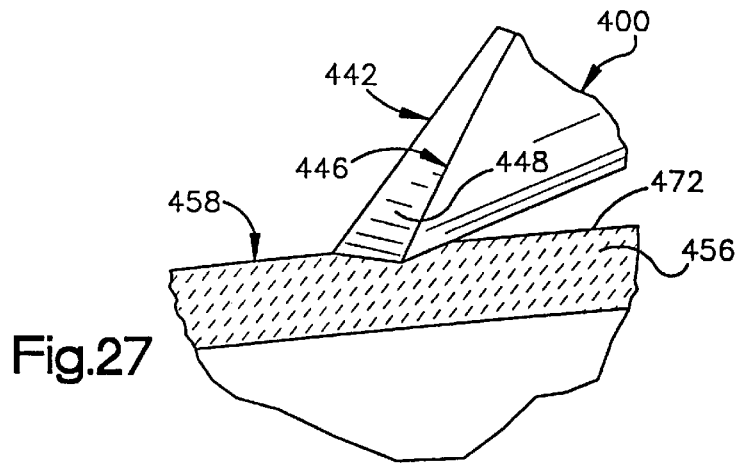
FIG. 27 is an enlarged fragmentary schematic illustration of a portion of FIG. 26 further illustrating the relationship between the pointed end portion of the cannula and the side wall of the blood vessel.

The cannula 400 can be used to establish communication with the interior of a blood vessel in a human body for an intravenous infusion. When this is to be done, the pointed end portion 442 of the cannula 400 is used to pierce an imperforate surface area on the skin 454 (FIG. 25) of a human body. After penetrating body tissue 460 beneath the skin, the pointed end portion 446 of the cannula 400 pierces an imperforate surface area on a side wall 456 of a vein or blood vessel 458 (FIGS. 26, 27 and 28). Thus, the cannula 400 is used to initiate the formation of openings in the skin 454 and side wall 456 of the blood vessel 458 at locations where there is no naturally occurring opening and without the necessity of making an incision prior to insertion of the cannula. An intravenous infusion of a suitable liquid preparation can then be conducted through the cannula 400 into the vein.

Figure 25:
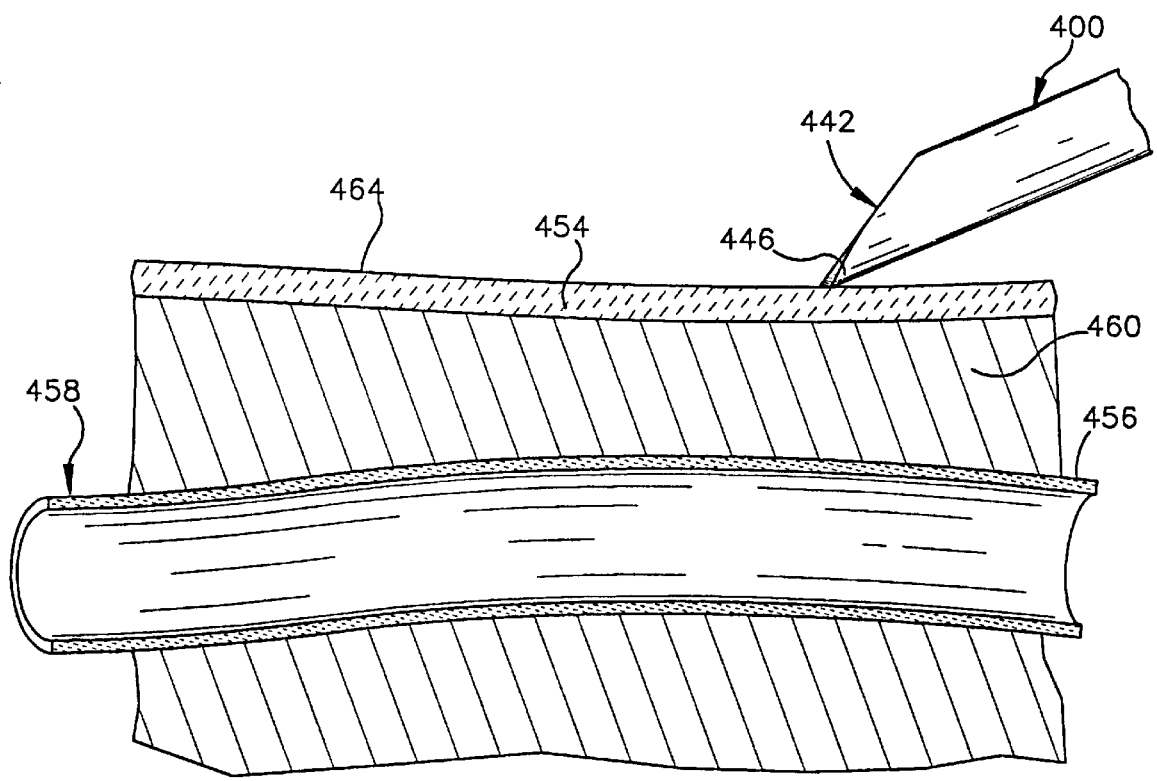
FIG. 25 is an enlarged fragmentary schematic illustration depicting the relationship between the contracted cannula of FIGS. 21–23 and body tissue immediately prior to insertion of the contracted cannula into the body tissue.

When the cannula 400 is to be inserted into the blood vessel 458 for an intravenous infusion or other purpose, the apex 446 of the pointed end portion 442 of the contracted cannula 400 is first pressed against an outer side surface 464 of the skin 454 (FIG. 25). Engagement of the end face 424 of the core 410 of the wire 404 which extends through the apex 446 of the pointed end portion 442 (FIGS. 21 and 23) of the cannula 400 punctures the outer side surface 464 of the skin 454 under the influence of force transmitted axially through the cannula 400. If desired, the pointed end portion 442 of the cannula 400 could have the sheath 402 configured in such a manner, that is, by elimination of the bevelled surface 448, so as to have the sheath itself initiate the formation of the opening in the skin 464. However, it is preferred to use the relatively sharp leading end portion of the core 410 of the wire 404 which extends through the apex 446 of the pointed end portion 442 (FIGS. 21 and 23) of the contracted cannula 400 to initiate the formation of the opening in the skin 454.

As the axially tapered pointed end portion 442 of the contracted cannula 400 pierces the skin 454, the size of the opening in the skin is increased. A cylindrical outer side surface 468 of the sheath 402 (FIGS. 25 and 26) enters the opening in the skin. At this time, the cannula 400 is in the contracted condition of FIG. 22. Therefore, a relatively small opening in the skin 454 can accommodate the cannula 400.

After the cannula 400 has pierced the skin 454, the cannula is pressed toward the blood vessel 448 and pierces the body tissue 460 (FIG. 26). The cannula 400 is moved through the body tissue 460 until the pointed end portion 446 of the cannula 400 engages the side wall 456 of the blood vessel 458. The pointed leading end portion 442 of the cannula 400 is then pressed firmly against the side wall 456 of the blood vessel 458 (FIG. 27).

The axial force transmitted through the contracted cannula 400 causes the axially tapered leading end of the core 410 of the wire 404 which extends through the apex 446 (FIG. 21) of the pointed end portion 442 of the cannula to initiate the formation of an opening at an imperforate outer side surface 472 (FIG. 27) of the side wall 456 of the blood vessel 458. Continued axial movement of the cannula 400 results in the leading end portion 442 of the cannula piercing the side wall 456 of the blood vessel 456. Since the cannula 400 is in the contracted condition of FIG. 22 when the side wall 456 of the blood vessel 458 is pierced, a relatively small opening 476 is formed in the side wall 456 of the blood vessel 456 by the cannula 400.

Although the cannula 400 is shown in FIG. 25 as being oriented with its longitudinal central axis at an angle of approximately 30° relative to the outer side surface 464 of the skin 454 as the skin is pierced, it is contemplated that it may be desired to have the cannula oriented at an angle of approximately 45° relative to the outer side surface 464 of the skin 454 when the skin is pierced by the cannula. In addition, in FIG. 26, the cannula is shown as being oriented relative to the blood vessel 458 with the longitudinal central axis of the cannula extending at an angle of approximately 30° relative to the outer side surface 472 of the blood vessel 458. It is contemplated that it may be desired to have the cannula oriented at a smaller angle relative to the outer side surface 472 of the blood vessel 458 as the blood vessel is pierced. Thus, there may be an angle of only 15° between the longitudinal central axis of the cannula 400 and the surface 472 of the blood vessel 458 as the blood vessel is pierced by the cannula 400. Reducing the angle between the longitudinal central axis of the cannula 400 and the outer side surface 472 of the blood vessel 458 prior to piercing the blood vessel facilitates piercing the side wall 456 of the blood vessel 458 without pushing the cannula 400 clear through the blood vessel.

Once the contracted cannula 400 has been inserted into the blood vessel 458, the cannula is moved axially along the blood vessel (FIG. 28) to increase the telescopic relationship between the blood vessel and the cannula. Although the cannula 400 has been shown in FIG. 28 as being inserted for only a relatively a small distance into the blood vessel 458, it is contemplated that the cannula may be inserted for a substantial distance into the blood vessel. Thus, the cannula 400 may be moved along the blood vessel 458 to another vessel, such as a sac or organ.

Since the cannula 400 is in the contracted condition of FIG. 22, the cannula will have a small outside diameter (FIG. 29) and will be relatively easy to move along the blood vessel 458. The contracted cannula 400 will form a relatively small opening 476 in the side wall 456 of the blood vessel 458. It is contemplated that the contracted cannula 400 may have a sufficiently large central passage 406 for some purposes. For example, an intravenous injection of a small dose of medicine could be made through the contracted cannula 400 if desired. However, it is believed that the cannula 400 will be advantageously used in circumstances requiring a relatively large passage 406 for communication with the interior of the blood vessel 458 and/or a vessel connected with the blood vessel 458.

When a relatively large passage 406 is required through the cannula 400 to communicate with the interior of the blood vessel 458, the cannula 400 is expanded from the contracted condition of FIG. 22 to the expanded condition of FIG. 24 by the sequential insertion of members into the cannula. Thus, the first tubular member 430 (FIG. 24) is inserted into the cannula 400 to increase the diameter of the outer side surface 468 of the cannula and to effect a relatively small radial expansion of the side wall 456 of the blood vessel 458.

As the cannula 400 is expanded, the outer side surface 468 of the cannula is pressed against edge portions of the opening 476 to increase the size of the opening. In addition, the outer side surface 468 of the cannula 400 is pressed against the edge portions of the opening in the skin 454 to increase the size of the opening in the skin. Of course, the outer side surface 468 of the cannula 400 also applies force against the inner side surface of the blood vessel 458 to expand the blood vessel.

The tubular member 436 (FIGS. 24, 30 and 31) is then inserted into the cannula 400 to further expand the cannula and the blood vessel 458. As the cannula 400 is expanded, force is transmitted from the outer side surface 468 of the cannula to an inner side surface of the blood vessel 458 to radially expand the blood vessel. In addition, the openings in both the blood vessel 458 and skin 454 are expanded.

Figure 30:
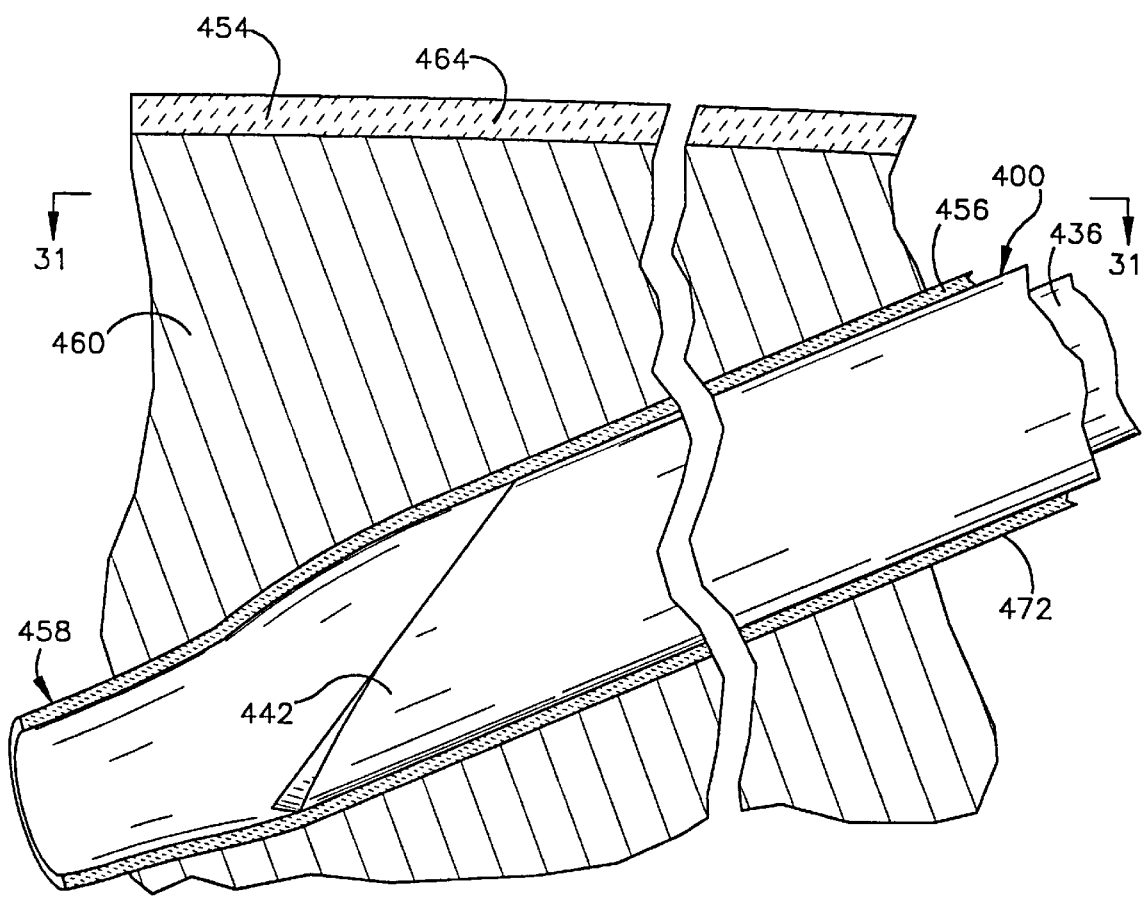
FIG. 30 is a fragmentary schematic illustration, generally similar to FIG. 28, illustrating the relationship between the cannula and the blood vessel when the cannula is in an expanded condition.
Figure 31:
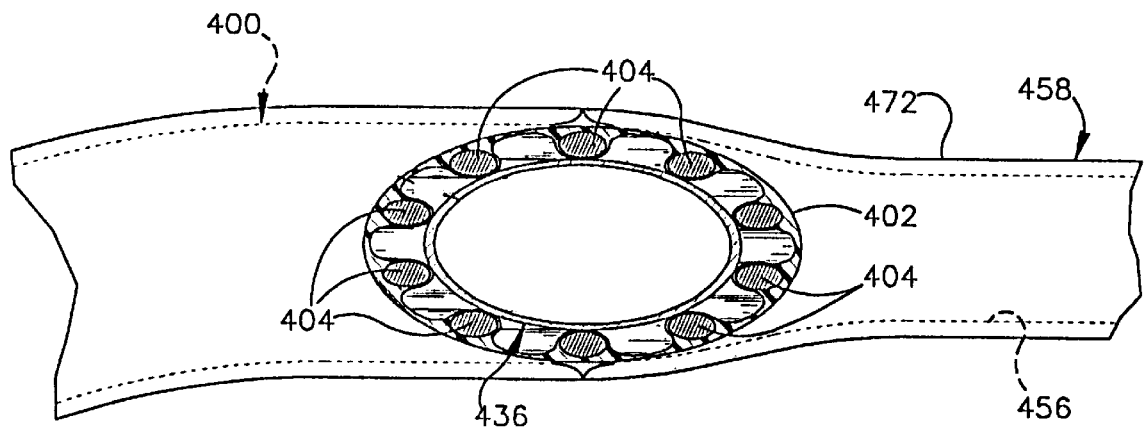
FIG. 31 is a schematic illustration, similar to FIG. 29, and taken generally along the line 31—31 of FIG. 30.

Due to the viscoelastic characteristics of the side wall 456 of the blood vessel 458, the diameter of the blood vessel can be substantially increased by expanding the cannula 400 from the contracted condition of FIGS. 28 and 29 to the expanded condition of FIGS. 30 and 31. Of course, expanding the side wall 456 of the blood vessel 458 enable fluid (liquid) to be conducted at a relatively high flow rate into the blood vessel. The fluid is conducted through the tubular member 436 and the cannula 400 into the blood vessel 458. In addition, expansion of the side wall 456 of the blood vessel 458 along with the cannula 400 enables surgical instruments and/or optical instruments to be inserted through the cannula into the blood vessel. Of course, if the contracted cannula 400 is moved along the blood vessel into another vessel, such as a sac or organ, before being expanded, the surgical instruments inserted through the central passage of the expanded cannula can be used within the sac or other body part.

In the embodiment of the invention illustrated in FIGS. 21–31, the core 410 of the wire 404 which extends into the apex 446 of the pointed end portion 442 is co-extensive with the sheath 402. In the embodiment of the invention illustrated in FIG. 32, the core of the wire which extends into the apex of the pointed end portion of the cannula extends beyond the sheath of the cannula to facilitate engagement of the core with the wire with body tissue. Since the embodiment of the invention illustrated in FIG. 32 is generally similar to the embodiment of the invention illustrated in FIGS. 21–31, similar numerals will be utilized to designate similar components, the suffix letter "b" being associated with the numerals of FIG. 32 to avoid confusion.

Figure 32:
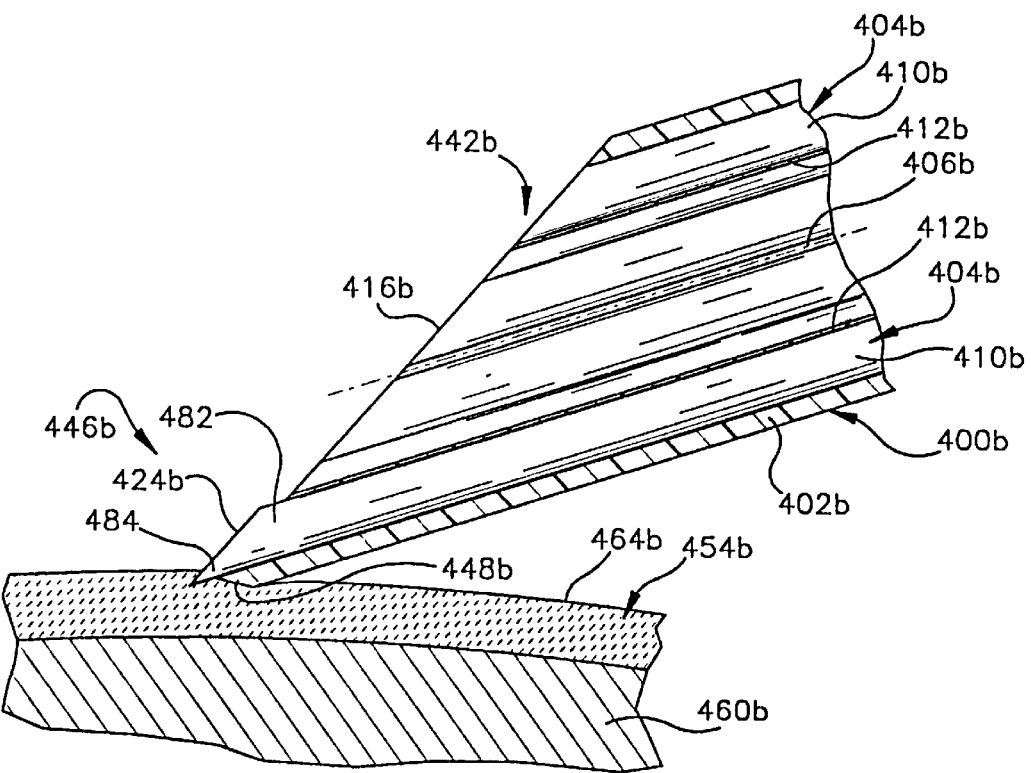
FIG. 32 is an enlarged schematic illustration, generally similar to FIG. 25, illustrating the relationship between another embodiment of the cannula and the skin of a patient immediately prior to piercing of the skin of the patient with the cannula.

In the embodiment of the invention illustrated in FIG. 32, the cannula 400b has a cylindrical sheath 402b which encloses a plurality of longitudinally extending wires 404b. Each of the wires 404b has a linear core 410b which is enclosed by a jacket 412b. The jacket 412b is integrally formed as one piece with the sheath 402b and cooperates with the sheath to enclose one of the cores 410b. The pointed end portion 442b has a circular opening 416b.

At an apex 446b of the pointed end portion 442b, a core 410b of one of the wires 404b extends past the bevelled outer edge surface 448b of the sheath 402b. Thus, an end portion 482 of the core 410b of the wire 404b extends past the opening 416b to the central passage 406b through the cannula 400b. The outwardly projecting core 410b has a pointed end portion 484 which projects axially outwardly from the sheath 402b.

When the contracted cannula 400b is to be used to form an opening in skin 454b, the pointed end portion 484 of the wire core 410b engages the outer side surface 464b of the skin before the sheath 402b engages the skin. This results in the sharp outer end portion 484 of the core 410b piercing the outer side surface 464b of the skin 454b before the skin is engaged by the sheath 402b. By piercing the outer side surface 464b of the skin 454b with the pointed end portion 484 of the core 410b, the forming of an opening in the skin by the contracted cannula 400b is facilitated.

In the embodiment of the invention illustrated in FIGS. 21–31, the cannula 400 has a circular cross sectional configuration as viewed in a plane extending perpendicular to a longitudinal central axis 418 of the cannula (FIG. 22). It is contemplated that the cross sectional area of the cannula may be maximized by forming the cannula with an oval cross sectional configuration as viewed in a plane extending perpendicular to a longitudinal central axis of the cannula.

In addition, in the embodiment of the invention illustrated in FIGS. 33 and 34, the cannula is expanded under the influence of fluid pressure rather than by inserting members into the cannula in the manner described in conjunction with FIG. 24. Of course, if desired, members having an oval cross sectional configuration could be inserted into the cannula of FIGS. 33 and 34 to expand the cannula. Since the cannula of FIGS. 33 and 34 have the components of the same construction as the components of the cannula of FIGS. 21–31, similar numerals will be utilized to identify similar components, the suffix letter "c" being associated with the numerals of FIGS. 33 and 34 to avoid confusion.

The cannula 400c is inserted into a blood vessel 458c in the manner illustrated in FIGS. 33 and 34. The cannula 400c includes an elastic sheath 402c. The sheath 402c encloses longitudinally extending wires 404c. The wires 404c include cores 410c and jackets 412c. The jackets 412c are integrally formed as one piece with the sheath 402c.

In accordance with one of the features of the embodiment of the invention illustrated in FIGS. 33 and 34, the cannula 400c has an oval configuration (FIG. 34) as viewed in across sectional plane extending perpendicular to a longitudinal central axis of the cannula. By forming the cannula 400c with an oval configuration, the area of a central passage 406c through the cannula tends to be maximized.

When the cannula 400c is inserted into a blood vessel 458c (FIG. 33), the major axis of the oval cross section of the cannula is aligned with the longitudinal central axis of the blood vessel 458c at the location where the cannula extends through an opening in the side wall of the blood vessel. Thus, the longitudinal central axis of the blood vessel 458c is disposed in the same plane as the major cross sectional axis of the oval cross section (FIG. 34) of the cannula. The minor axis of the oval cross section of the cannula extends radially relative to the blood vessel 458c.

By aligning the major axis of the oval cross section of the cannula 400c with the longitudinal central axis of the blood vessel 458c, the major axis of the opening formed in the blood vessel 458c extends longitudinally along the side wall 456c of the blood vessel (FIG. 33). Thus, when the cannula 400c pierces the outer side surface 472c of the blood vessel 458c, the opening which is formed in the outer side surface 472c of the blood vessel 458c is relatively long in a lengthwise direction along the blood vessel. However, the opening formed in the outer side surface 472c of the blood vessel 458c is relatively small in a direction extending circumferentially around the blood vessel.

It should be understood that when the cannula 400c pierces the side wall 456c of the blood vessel 458c, the cannula is in a contracted condition in which it has a substantially smaller cross sectional configuration than is illustrated in FIG. 33. Thus, the relationship of the contracted cannula 400c to the blood vessel 458c when the cannula pierces the side wall 456c of the blood vessel is similar to the relationship illustrated in FIG. 29 for the cannula 400 to the blood vessel 458. However, the contracted cannula 400c will have a major cross sectional axis which is aligned with the longitudinal central axis of the blood vessel 458c (FIG. 33). The minor cross sectional axis of the contracted cannula 400c will have an extent which is equal to the diameter of the contracted cannula 400 of FIGS. 21–31.

In accordance with another feature of the present invention, the cannula 400c is expanded throughout its length under the influence of fluid pressure. A pump 490 is connected with the central passage 406c in the cannula 400c through a valve 492 and a conduit 494. Relatively high pressure fluid is discharged from the pump 490 through the valve 492 and conduit 494 into the central passage 406c in the contracted cannula 400c. This fluid pressure is applied against an inner side surface of the sheath 402c and the wires 404c.

The fluid pressure inside the cannula 400c is effective to cause the elastic material of the sheath 402c to expand from a contracted condition to an expanded condition. As this occurs, the size of the opening formed in the viscoelastic material of the blood vessel 458c is enlarged. In addition, the outer side surface of the cannula 400c presses against the inner side surface of the side wall 456c to expand the blood vessel 458c downstream from the location where the cannula enters the blood vessel.

The fluid from the pump 490 forms an intravenous infusion of a liquid solution to the blood vessel 458c. Of course, if the cannula 400c is to be used to provide access for surgical tools and/or optical instruments to the interior of the blood vessel 458c or with a part of the body connected with the blood vessel, the cannula 400c could be expanded by using tubular members having an oval cross sectional configuration in the manner described in conjunction with FIG. 24. It should be understood that fluid pressure may be used to expand the cannula 400 of FIGS. 21–31 if desired.

In the embodiment of the invention illustrated in FIGS. 21–31, the end face or surfaces 424 on the core 410 of the wires 404 are exposed (FIGS. 22 and 23). Thus, the jackets 412 enclose the cores 410 throughout the length of the cores. However, in the embodiment of the invention illustrated in FIGS. 21–31, the jackets 412 do not cover the end surfaces 424 of the cores 410. Therefore, the end surfaces 424 of the cores 410 are exposed at the pointed end portion 442 of the cannula 400.

In the embodiment of the invention illustrated in FIG. 35, the jackets around the cores cover the end surfaces of the cores. Since the embodiment of the invention illustrated in FIG. 35 is generally similar to the embodiment of the invention illustrated in FIGS. 21–31, similar components will be identified with similar numerals, the suffix letter "d" being associated with the numerals of FIG. 35 to avoid confusion.

In the embodiment of the invention illustrated in FIG. 35, a cannula 400d includes an elastic sheath 402d. The sheath 402d encloses a plurality of longitudinally extending wires 404d. The cannula 400d has a longitudinally extending central passage 406d.

Each of the wires 404d includes a core 410d and a jacket 412d which extends around the core 410d. Each of the jackets 412d is integrally formed as one piece with the sheath 402d. Each of the jackets 412d extends between opposite ends of the sheath 402d.

In accordance with a feature of the embodiment of the invention illustrated in FIG. 35, the jacket 412d around each of the cores 410d extends across an axially outer end face 424d of a core 410d. Thus, at a pointed end portion 442d of the cannula 400d, the cores 410d of the wires 404d are completely enclosed by cooperation between the jackets 412d and the sheath 402d. The jackets 412d include end sections 502 which extend across the end surfaces 424d of the cores 410d of the wires 404d. This results in the cannula 400d having a pointed end portion 442d with an apex 446d which is formed by the sheath 402d.

When the cannula 404d is to pierce body tissue, the pointed apex 446d of the end portion 442d of the cannula engages the body tissue. In the embodiment of the invention illustrated in FIG. 35, the apex 446d of the pointed end portion 442d is formed by the elastic material of the sheath 402d and jackets 412d. Thus, the cores 410d do not engage the body tissue as the cannula hood is inserted into the body tissue.

When the cannula 400d is to be inserted into body tissue, the pointed end of the sheath 402d initiates the formation of the opening in the body tissue. The wires 404d stiffen the elastic material of the sheath 402d to enable force to be transmitted through the cannula 400d to the axially outer end of the sheath.

In the embodiment of the invention illustrated in FIGS. 18–20, an end portion of the cannula 300 is expandable outward of the outer sheath 308 and the inner wall 310. In the embodiment of the invention illustrated in FIGS. 36, 37 and 38, the cannula also has an end portion which is expandable outward of an outer side surface of a sheath to engage body tissue. Since the embodiment of the invention illustrated in FIGS. 36, 37 and 38 is generally similar to the embodiment of the invention illustrated in FIGS. 21–31, similar numerals will be utilized to designate similar components, the suffix letter "e" being associated with the numerals of FIGS. 36, 37 and 38 to avoid confusion.

Figure 36:
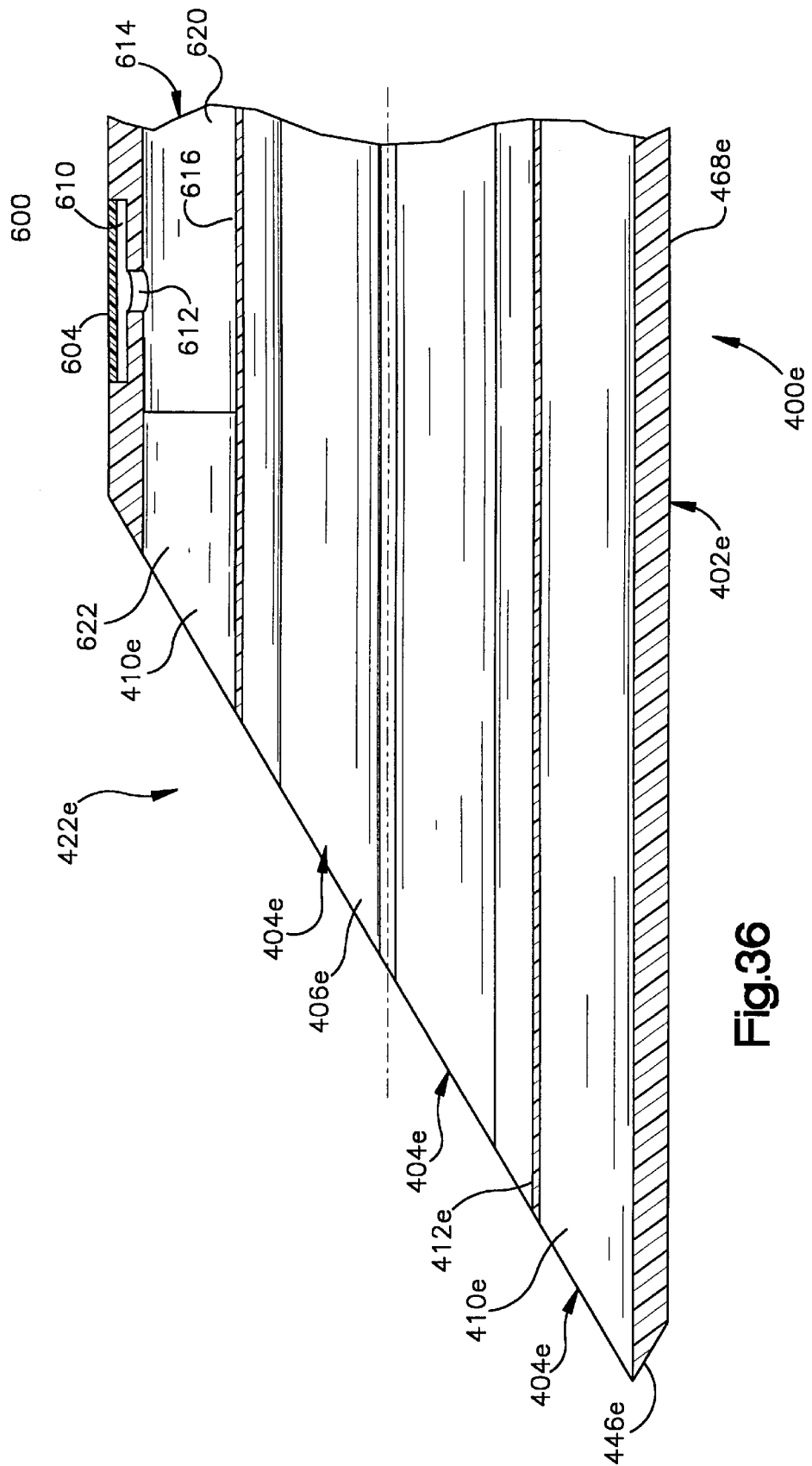
FIG. 36 is a fragmentary sectional view, generally similar to FIG. 21, illustrating a pointed end portion of another embodiment of the cannula.
Figure 37:
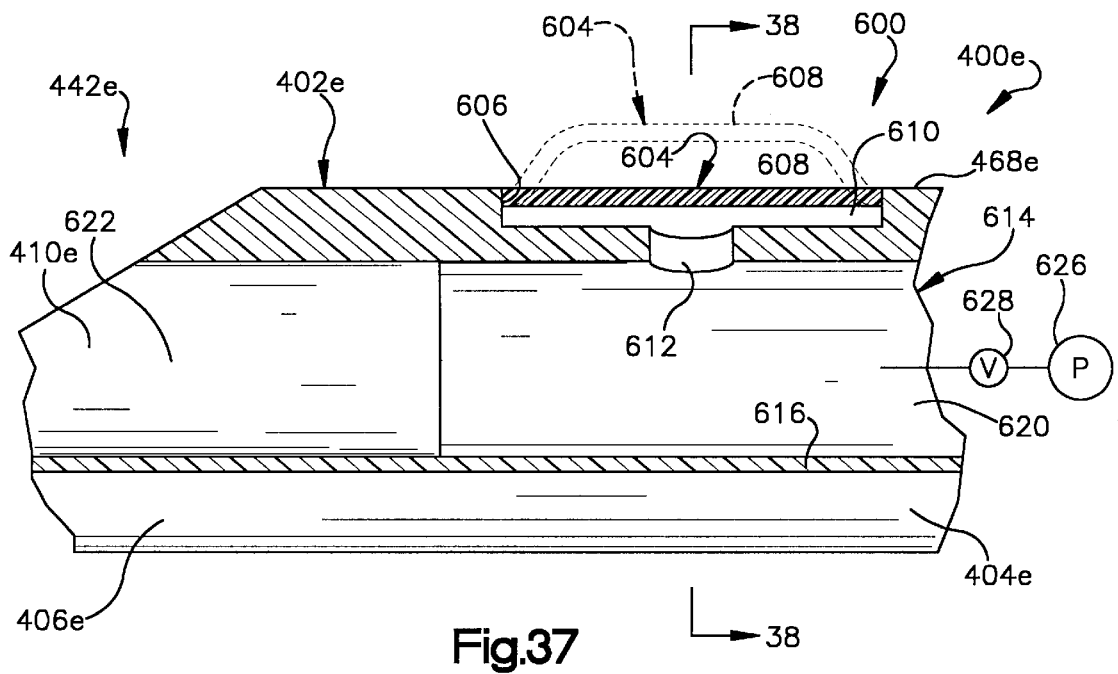
FIG. 37 is an enlarged fragmentary sectional view of a portion of FIG. 36 illustrating the construction of an end portion of the cannula which is expandable when the cannula is in the expanded condition of FIG. 24.
Figure 38:
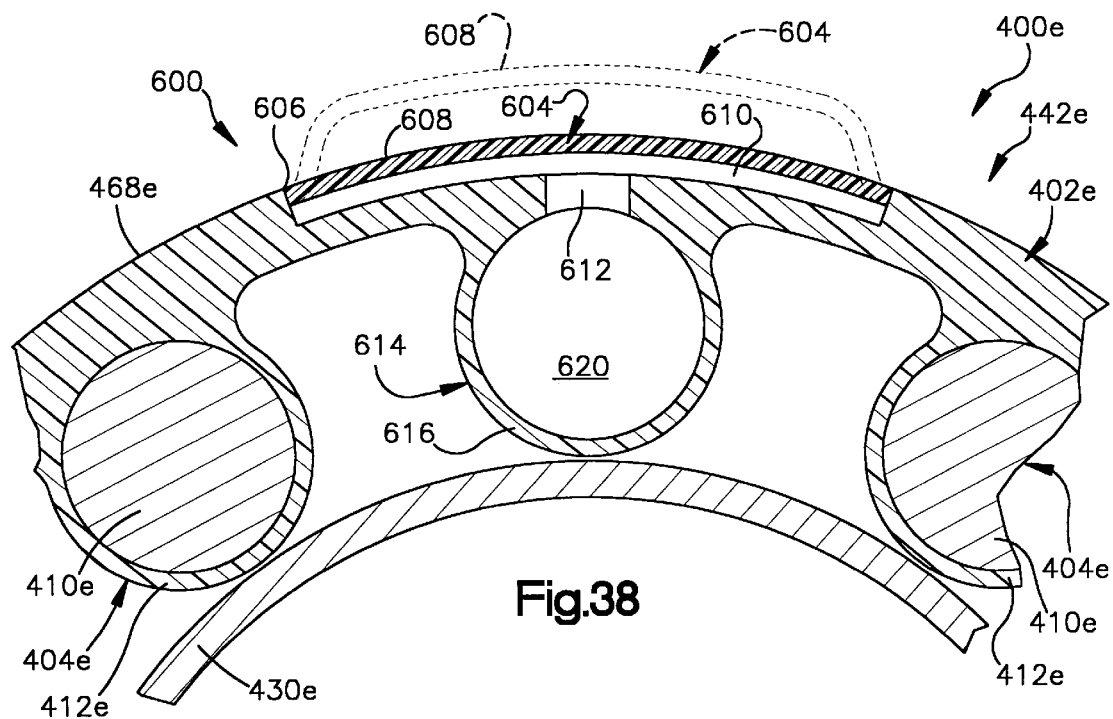
FIG. 38 is a sectional view, taken generally along the line 38—38 of FIG. 37, further illustrating the construction of the end portion of the cannula.

In the embodiment of the invention illustrated in FIGS. 36–38, a cannula 400e has an elastic sheath 402e. The sheath 402e encloses a plurality of longitudinally extending wires 404e. The cannula 400e has a longitudinally extending central passage 406e.

Each of the wires 404e includes a core 410e and a jacket 412e (FIG. 38). Each of the jackets 412e is integrally formed as one piece with the sheath 402e. Each of the jackets 412e extends between opposite ends of the sheath 402e.

When the contracted cannula 400e is to be used for form an opening in body tissue, the pointed end portion 442e (FIG. 36) of the cannula 400e engages the body tissue. The apex 446e of the pointed end portion 442e penetrates the body tissue and initiates the formation of an opening in the body tissue at an imperforate surface area on the body tissue. The initiating of the opening in the body tissue is facilitated by having an exposed relatively sharp end portion of a core 410e of a wire 404e which extends through the apex 446e of the pointed end portion 442e of the contracted cannula 400e engage the body tissue to initially cut the imperforate surface area of the body tissue. The leading edge portions of the sheath 402e disposed adjacent to opposite sides of the wire 404e through the apex 446e of the cannula 400e are then effective to sever body tissue to increase the size of the opening in the body tissue.

As the contracted cannula 400e is further inserted into the body tissue, the leading end portions of additional wires 404e and leading edges of segments of the sheath 402e disposed between the wires sever the body tissue to increase the size of the opening. The size of the opening is increased until it is large enough to accept the cylindrical outer side surface 468e of the cannula 400e when the cannula is in the contracted condition.

Once the cannula 400e has been inserted for a desired distance into the body tissue, the cannula is expanded by inserting a tubular cylindrical member 430e (FIG. 38) into the contracted cannula 400e. As the tubular member 430e is inserted into the contracted cannula, the sheath 402e is resiliently expanded and the cross sectional size of the longitudinally extending array of wires 404e is increased. Of course, the cannula 400e could be further expanded by the insertion of a second tubular member, corresponding to the tubular member 436 of FIG. 24.

In accordance with a feature of this embodiment of the invention, once the cannula 400e has been positioned in body tissue, a portion 600 of the pointed end portion 442e of the cannula is expandable outward of an outer side surface 468e of the sheath 402e. Thus, the portion 600 is expandable from the configuration shown in solid lines in FIGS. 37 and 38 to the configuration shown in dashed lines in FIGS. 37 and 38. This enables the portion 600 of the cannula 400e to engage body tissue and hold the cannula in place in the body tissue.

When the pointed end portion 442e of the cannula 400e is inserted into body tissue, for example, into a vein, both the cannula sheath 402e and the portion 600 of the cannula are contracted. When the cannula 400e has been inserted a desired distance into the vein, the cannula sheath 402e is expanded by either fluid pressure or by insertion of the tubular member 430e. The portion 600 of the cannula 400e is then expanded radially outward from the cylindrical sheath 402e to grip the inner side surface of the vein. It is contemplated that in certain circumstances it may not be necessary to expand the sheath 402e and the portion 600 will be expanded while the sheath is contracted.

The portion 600 of the cannula 400e includes a resilient panel 604 (FIGS. 37 and 38) which is disposed in a rectangular recess 606 formed in the sheath 402e. When the portion 600 is in the contracted condition shown in solid lines in FIGS. 37 and 38, an arcuate outer side surface 608 of the panel 604 is aligned with the outer side surface 468e of the sheath 402e.

The panel 604 cooperates with the sheath 402e to form a variable volume chamber 610 in the side wall of the sheath. The panel 604 is formed of a polymeric material having a substantially greater elasticity than the material of the sheath 402e. The elasticity of the material of the panel 604 enables the panel to be resiliently expanded from the position shown in solid lines in FIGS. 37 and 38 to the position shown in dashed lines and subsequently retracted.

The chamber 610 is connected in fluid communication, through an opening 612 in the sheath 402e with a conduit 614. The conduit 614 has a side wall 616 which is integrally formed with the sheath 402e. The side wall 616 of the conduit 614 and the sheath 402e cooperate to form a cylindrical passage 620 which extends between opposite ends of the sheath 402e. An axially outer or distal end portion of the conduit 620 is blocked by a pointed segment 622 of a metal core 410e (FIG. 37) of a wire. The core 410e is fixedly secured, by adhesive, in the passage 620 to block fluid flow through the outer end of the passage.

The passage 620 extends to the opposite or proximal end of the cannula 400e. The proximal end of the passage 620 is connected with a pump 626 (FIG. 37) through a valve 628. Since the segment 622 of a wire core 410e blocks the axially outer or distal end of the passage 620, any fluid which flows through the valve 628 into the passage 620 must flow into the chamber 610.

Once the sheath 402e of the cannula 400e has been expanded (FIG. 38) by the insertion of a tubular member 430e or by fluid pressure, fluid pressure is conducted through the passage 620 to the chamber 610 to expand the chamber 610. Thus, the valve 628 (FIG. 37) is actuated to connect the pump 626 in fluid communication with the passage 620. Fluid flows from the pump 626 through the passage 620 and opening 612 to the chamber 610. The fluid pressure in the chamber 610 moves the panel 604 outwardly from the position shown in solid lines in FIGS. 37 and 38 to the position shown in dashed lines. As this occurs, the panel 604 grips body tissue to retain the cannula 400e against movement relative to the body tissue.

In the embodiment of the invention illustrated in FIG. 38, the side wall 616 of the conduit 614 is formed in the same manner and has the same size as the jackets 412e of the wires 404e. Thus, when the sheath 402e is formed with the wires 404e, a removable core is provided at the location where the passage 620 is to be formed. Once the material of the jackets 412e and the side wall 616 of the conduit 614 has solidified, the core in the side wall 616 of the conduit 614 is removed to leave the passage 620. The end segment 662 (FIG. 37) of one of the cores 410e is then inserted into the passage 620 to block the axially outer end of the passage.

This results in the conduit 614 being disposed in the longitudinal array of wires 404e and having the same size as one of the wires. When the tubular member 430e (FIG. 38) is inserted into the cannula, the outer side surface of the tubular member slides along the side wall 616 of the conduit 614 in the same manner as in which the tubular member slides along the jackets 412e of the wires 404e. Therefore, force is transmitted from the tubular member 430e through the conduit 614 to the sheath 402e to expand the sheath when the tubular member is inserted into the cannula 400e.

During construction of the cannula 400e, the recess 606 is formed in the side wall of the sheath 402e. After the opening 612 between the passage 620 and the recess 606 in the sheath 402e has been formed, the panel 604 is electron beam welded or otherwise secured to the sheath.

From the above description of the invention, those skilled in the art will perceive improvements, changes and modifications in the invention. Such improvements, changes and modifications within the skill of the art are intended to be covered by the appended claims.

Having described the invention, the following is claimed:

1. A cannula comprising a longitudinally extending tubular sheath having a main passage, a variable volume chamber connected with said sheath and disposed adjacent to one end portion of said sheath, said one end portion of said sheath and said variable volume chamber being insertable into body tissue, said variable volume chamber being expandable under the influence of fluid pressure from a contracted condition to an extended condition in which said variable volume chamber projects outward of a side surface of said sheath when said one end portion of said sheath and said variable volume chamber are disposed in body tissue to retard withdrawal of said one end portion of said sheath from body tissue when said one end portion of said sheath is disposed in body tissue, a plurality of wires which are enclosed by said sheath and extend along an inner side of said sheath, and a conduit which is enclosed by said sheath and extends along an inner side of said sheath to said variable volume chamber, said conduit being disposed between adjacent wires of said plurality of wires, said conduit being adapted to be connected in fluid communication with a source of fluid pressure to enable said conduit to conduct fluid pressure to said variable volume chamber to effect expansion of said variable volume chamber from the contracted condition to the extended condition when said one end portion of said sheath and said variable volume chamber are disposed in body tissue.

2. A cannula as set forth in claim 1 wherein said one end portion of said sheath has a pointed configuration to pierce body tissue.

3. A cannula as set forth in claim 1 wherein said wires have exposed end portions at said one end portion of said sheath to enable said end portions of said wires to engage body tissue during insertion of said one end portion of said sheath and the variable volume chamber into body tissue.

4. A cannula as set forth in claim 1 wherein said sheath has a leading end surface which engages body tissue at locations between adjacent wires during insertion of said one end portion of said sheath and the variable volume chamber into body tissue.

5. A cannula as set forth in claim 1 wherein each of said wires includes a longitudinally extending core and a jacket of polymeric material, said jacket of polymeric material being connected with said sheath, said conduit being formed of polymeric material and having the same configuration as one of said jackets, said conduit being connected with said sheath at a location between a pair of said wires.

6. A cannula as set forth in claim 5 wherein an end portion of a core of at least one of said wires is exposed at said one end portion of said sheath to enable said core of said one wire to engage body tissue during insertion of said one end portion of said sheath into body tissue.

7. A cannula as set forth in claim 5 wherein an end portion of a core of at least one of said wires is completely enclosed by said sheath and said jacket at said one end portion of said sheath to block engagement of body tissue with said core of said one wire during insertion of said one end portion of said sheath into body tissue.

8. A cannula as set forth in claim 5 wherein an end portion of a core of at least one of said wires extends beyond said one end portion of said sheath to enable said core of said one wire to engage body tissue ahead of said sheath during insertion of said one end portion of said sheath into body tissue.

9. A cannula as set forth in claim 1 wherein at least a portion of each of said wires is integrally formed as one piece with said sheath to interconnect said wires and said sheath, said conduit being integrally formed as one piece with said sheath to interconnect said conduit and said sheath.

10. A cannula as set forth in claim 1 wherein each of said wires includes a longitudinally extending core having generally circular cross sectional configuration and a jacket which at least partially encloses said core, said jacket being integrally formed as one piece with said sheath to interconnect said core and said sheath.

11. An expandable cannula as set forth in claim 1 wherein each of said wires includes a longitudinally extending core formed of metal and a jacket which at least partially encloses said core, said jacket, said sheath and said conduit being integrally formed as one piece of polymeric material.

12. A cannula as set forth in claim 1 further including an insert insertable into the main passage in said tubular sheath to effect expansion of said tubular sheath from a first cross sectional area to a second cross sectional area, said second cross sectional area being larger than said first cross sectional area, each of said wires and said conduit having an outer side surface which is engageable by said insert to enable each of said wires and said conduit to transmit force from said insert to said sheath.

13. A cannula as set forth in claim 12 wherein said outer side surface of each of said wires and said conduit are integrally formed as one piece with said sheath.

14. A cannula as set forth in claim 1 wherein said wires and said conduit have longitudinally extending outer side surface areas forming contact surfaces for a member inserted into the main passage in said tubular sheath, each of said wires and said conduit blocking engagement of a longitudinally extending portion of said sheath with the member inserted into the main passage in said sheath.

15. A cannula as set forth in claim 14 wherein said longitudinally extending outer side surface areas on said wires and said conduit are integrally formed as one piece with said sheath.

16. A cannula as set forth in claim 1 wherein said wires and said conduit have parallel longitudinal central axes which extend parallel to a longitudinal central axis of said sheath.

17. A cannula as set forth in claim 1 wherein said conduit is integrally formed as one piece with said sheath.

18. A cannula as set forth in claim 1 wherein at least a portion of each of said wires is integrally formed as one piece with said sheath.

19. A cannula comprising a longitudinally extending tubular sheath having a main passage, a variable volume chamber connected with said sheath and disposed adjacent to one end portion of said sheath, a plurality of wires which are enclosed by said sheath and extend along an inner side of said sheath, surface means disposed on said one end portion of said sheath and on end portions of said wires for piercing body tissue, and a conduit which is enclosed by said sheath extends along an inner side of said sheath to said variable volume chamber, said conduit being adapted to be connected in fluid communication with a source of fluid pressure to enable said conduit to conduct fluid pressure to said variable volume chamber to effect expansion of said variable volume chamber from the contracted condition to the extended condition when said one end portion of said sheath and said variable volume chamber are disposed in body tissue.

20. A cannula as set forth in claim 19 wherein said conduit is integrally formed as one piece with said sheath.

21. A cannula as set forth in claim 19 wherein at least a portion of each of said wires is integrally formed as one piece with said sheath.

22. A cannula as set forth in claim 19 wherein said wires and said conduit have parallel longitudinal central axes which extend parallel to a longitudinal central axis of said sheath.

23. A cannula comprising a longitudinally extending tubular sheath formed of a material capable of being expanded from a contracted condition in which a longitudinally extending passage through the tubular sheath has a relatively small cross sectional size to an expanded condition in which the passage has a relatively large cross sectional size, a plurality of wires enclosed by said sheath, said wires being disposed in a longitudinally extending array along an inner side of said sheath, said longitudinally extending array of wires having a relatively small cross sectional size when said sheath is in the contracted condition and a relatively large cross sectional size when said sheath is in the expanded condition, said wires having longitudinal central axes which are disposed in a parallel relationship when said sheath is in the contracted condition and when said sheath is in the expanded condition, and a flexible portion is connected with said sheath and is expandable outward of an outer side surface of said sheath to engage body tissue when said sheath is in the expanded condition.

24. A cannula as set forth in claim 23 further including a fluid conduit enclosed by said sheath and connected in fluid communication with said flexible portion, said fluid conduit being disposed along the inner side of said sheath and having a longitudinal central axis which extends parallel to the longitudinal central axes of said wires.

25. A cannula as set forth in claim 23 wherein said flexible portion includes a chamber which is expandable relative to said sheath under the influence of fluid pressure, said cannula further including means for conducting fluid pressure to said chamber to expand said chamber while said sheath is in the expanded condition.

26. A cannula as set forth in claim 25 wherein said means for conducting fluid pressure to said chamber to expand said chamber includes a conduit which is integrally formed as one piece with said sheath.

27. A cannula as set forth in claim 26 wherein said wires have longitudinally extending outer side surface areas which are integrally formed as one piece with said sheath.

28. A cannula as set forth in claim 23 wherein said cannula includes a pointed end portion to pierce body tissue, said pointed end portion of said cannula being formed by an end portion of said sheath and by end portions of said wires.

29. A cannula as set forth in claim 23 wherein each of said wires has a core formed of a first material and a jacket which extends at least part way around said core and is formed of a material which is different than said first material, said cannula further including a fluid conduit which is disposed in the longitudinally extending array of wires and has a side wall formed of the same material as the jackets of said wires.

30. A cannula comprising a longitudinally extending tubular sheath formed of a material capable of being expanded from a contracted condition in which a longitudinally extending passage through the tubular sheath has a relatively small cross sectional size to an expanded condition in which the passage has a relatively large cross sectional size, a plurality of wires enclosed by and connected with said sheath, said wires being disposed in a longitudinal extending array along an inner side of said sheath, said longitudinally extending array of wires has a relatively small cross sectional size when said sheath is in the contracted condition and a relatively large cross sectional size when said sheath is in the expanded condition, a flexible portion is connected with said sheath and is expandable under the influence of fluid pressure to engage body tissue when said sheath is in the expanded condition, and a fluid conduit enclosed by and connected with said sheath and extending along an inner side of said sheath to said flexible portion, said conduit being effective to conduct fluid pressure to said flexible portion to effect expansion of said flexible portion, said conduit being spaced a first distance from a longitudinal central axis of said sheath when said sheath is in the contracted condition and being spaced a second distance from the longitudinal central axis of said sheath when said sheath is in the expanded condition, said second distance being greater than said first distance, said conduit being disposed between adjacent wires in said longitudinally extending array of wires when said sheath is in the contracted condition and when said sheath is in the expanded condition.

31. A cannula as set forth in claim 30 wherein said flexible portion includes a chamber which is expandable relative to said sheath under the influence of fluid pressure conducted to said chamber through said conduit.

32. A cannula as set forth in claim 30 wherein said conduit is integrally formed as one piece with said sheath.

33. A cannula as set forth in claim 32 wherein said wires have longitudinally extending outer side surface areas which are integrally formed as one piece with said sheath.

34. A cannula as set forth in claim 30 wherein said cannula has a pointed end portion to pierce body tissue, said pointed end portion of said cannula being formed by an end portion of said sheath and by end portions of said wires.

35. A cannula as set forth in claim 30 wherein said wires and said conduit have longitudinal central axes which extend parallel to a longitudinal central axis of said sheath.

36. A cannula comprising a longitudinally extending tubular sheath formed of a material capable of being expanded from a contracted condition in which a longitudinally extending passage through the tubular sheath has a relatively small cross sectional size to an expanded condition in which the passage has a relatively large cross sectional size, a plurality of wires enclosed by said sheath, said wires being disposed in a longitudinally extending array along an inner side of said sheath, said longitudinally extending array of wires having a relatively small cross sectional size when said sheath is in the contracted condition and a relatively large cross sectional size when said sheath is in the expanded condition, a flexible portion connected with said sheath and expandable outward of an outer side surface of said sheath to engage body tissue when said sheath is in the expanded condition, and surface means disposed on said sheath and on said wires for piercing body tissue when said sheath is in the contracted condition.

37. A cannula as set forth in claim 36 further including a fluid conduit enclosed by said sheath and connected in fluid communication with said flexible portion, said fluid conduit being disposed along the inner side of said sheath in the longitudinally extending array of wires.

38. A cannula as set forth in claim 36 wherein said flexible portion includes a chamber which is expandable relative to said sheath under the influence of fluid pressure, said cannula further including means for conducting fluid pressure to said chamber to expand said chamber while said sheath is in the expanded condition.

39. A cannula as set forth in claim 38 wherein said means for conducting fluid pressure to said chamber to expand said chamber includes a conduit which is integrally formed as one piece with said sheath.

40. A cannula as set forth in claim 36 wherein said wires have longitudinally extending outer side surface areas which are integrally formed as one piece with said sheath.

41. An expandable cannula as set forth in claim 36 wherein each of said wires has a core formed of a first material and a jacket which extends at least part way around said core and is formed of a material which is different than said first material, said cannula further including a fluid conduit which is disposed in the longitudinally extending array of wires and has a side wall formed of the same material as the jackets of said wires.

42. A cannula as set forth in claim 36 further including a conduit to conduct fluid pressure to said flexible portion to effect expansion of said flexible portion when said sheath is in the expanded condition, each of said wires includes a longitudinally extending outer side surface area which is integrally formed as one piece with said sheath, said conduit having a longitudinally extending outer side surface area which is integrally formed as one piece with said sheath, said conduit being connected with said sheath at a location between adjacent wires in said longitudinally extending array of wires.

43. A cannula as set forth in claim 36 further including a conduit to conduct fluid pressure to said flexible portion when said sheath is in the expanded condition, said conduit being effective to conduct fluid pressure to said flexible portion to effect expansion of said flexible portion, said conduit being spaced a first distance from a longitudinal central axis of said sheath when said sheath is in the contracted condition and being spaced a second distance from the longitudinal central axis of said sheath when said sheath is in the expanded condition, said second distance being greater than said first distance.

44. A cannula as set forth in claim 43 wherein said conduit is enclosed by said sheath and is disposed between adjacent wires in said longitudinally extending array of wires.

45. A cannula as set forth in claim 36 wherein said wires have longitudinal central axes which extend parallel to a longitudinal central axis of said sheath when said sheath is in the contracted condition and when said sheath is in the expanded condition.

\* \* \* \* \*